(12) United States Patent
Chappel et al.

(10) Patent No.: US 12,042,626 B2
(45) Date of Patent: Jul. 23, 2024

(54) STATUS INDICATOR OF A DRUG DELIVERY SYSTEM

(71) Applicant: Debiotech S.A., Lausanne (CH)

(72) Inventors: Eric Chappel, Lausanne (CH); Dimitry Dumont-Fillon, Lausanne (CH); Arnaud Belladon, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 851 days.

(21) Appl. No.: 16/969,201

(22) PCT Filed: Feb. 15, 2019

(86) PCT No.: PCT/IB2019/051237
§ 371 (c)(1),
(2) Date: Aug. 12, 2020

(87) PCT Pub. No.: WO2019/159121
PCT Pub. Date: Aug. 22, 2019

(65) Prior Publication Data
US 2020/0405954 A1    Dec. 31, 2020

(30) Foreign Application Priority Data

Feb. 16, 2018   (EP) ..................................... 18157250
Jul. 11, 2018   (EP) ..................................... 18182850
(Continued)

(51) Int. Cl.
*A61M 5/168*     (2006.01)
*A61M 5/142*     (2006.01)
*A61M 5/145*     (2006.01)

(52) U.S. Cl.
CPC .... *A61M 5/16854* (2013.01); *A61M 5/14224* (2013.01); *A61M 5/14593* (2013.01);
(Continued)

(58) Field of Classification Search
CPC ...... A61M 2205/3331; A61M 5/14224; A61M 5/14593; A61M 5/16854
See application file for complete search history.

(56) References Cited

U.S. PATENT DOCUMENTS 1,516,032 A * 11/1924 White ....................... F04B 3/00
                                                           417/498
3,370,754 A *  2/1968 Schumann ............ B01F 35/713
                                                           222/132
(Continued)

FOREIGN PATENT DOCUMENTS

EP         1403519 A1    3/2004
GB         2404031       1/2005
(Continued)

OTHER PUBLICATIONS

Office Action issued in Japanese Patent Application No. 2020-543070 dated Nov. 29, 2022.
(Continued)

*Primary Examiner* — Quynh-Nhu H. Vu
(74) *Attorney, Agent, or Firm* — NIXON & VANDERHYE

(57) ABSTRACT

The present disclosure relates to an indicator device which comprises one or several plungers inside an elongated cavity. Said indicator device, is intended to provide to the user at least one information related to the current status of a delivery system. The indicator device comprises at least one movable element configured to reach pre-determined positions in response to the status of the delivery system.

14 Claims, 35 Drawing Sheets

(30) Foreign Application Priority Data

| Dec. 21, 2018 | (EP) | 18215745 |
|---|---|---|
| Jan. 11, 2019 | (EP) | 19151323 |
| Jan. 11, 2019 | (EP) | 19151324 |
| Jan. 11, 2019 | (EP) | 19151325 |
| Feb. 6, 2019 | (EP) | 19155800 |

(52) U.S. Cl.
CPC . *A61M 2205/15* (2013.01); *A61M 2205/3331* (2013.01); *A61M 2205/50* (2013.01); *A61M 2205/583* (2013.01); *A61M 2205/587* (2013.01); *A61M 2205/8206* (2013.01)

(56) References Cited

U.S. PATENT DOCUMENTS

| 3,570,486 | A | * | 3/1971 | Engelsher | B01F 35/7137 |
| | | | | | 604/88 |
| 3,626,474 | A | | 12/1971 | Hammer | |
| 3,923,058 | A | * | 12/1975 | Weingarten | A61M 5/3129 |
| | | | | | 604/203 |
| 4,188,949 | A | * | 2/1980 | Antoshkiw | A61M 3/005 |
| | | | | | 604/199 |
| 5,205,820 | A | | 4/1993 | Kriesel | |
| 5,639,220 | A | * | 6/1997 | Hayakawa | F04B 7/045 |
| | | | | | 347/30 |
| 9,194,383 | B2 | * | 11/2015 | Knobel | F04B 15/02 |
| 9,833,565 | B2 | | 12/2017 | Magnenat | |
| 9,872,955 | B2 | | 1/2018 | Chappel | |
| 9,903,351 | B2 | * | 2/2018 | Gros-D'Aillon | F04B 1/00 |
| 2004/0115068 | A1 | | 6/2004 | Hansen | |
| 2005/0044964 | A1 | | 3/2005 | Oskouei | |
| 2006/0069382 | A1 | | 3/2006 | Pedersen | |
| 2008/0009836 | A1 | | 1/2008 | Fiering | |
| 2008/0118376 | A1 | * | 5/2008 | Verrilli | F04B 13/00 |
| | | | | | 417/385 |
| 2009/0035152 | A1 | | 2/2009 | Butterfield | |
| 2011/0118432 | A1 | | 5/2011 | Zhao | |
| 2011/0132480 | A1 | | 6/2011 | Chappel | |
| 2012/0048403 | A1 | | 3/2012 | Chappel | |
| 2012/0186509 | A1 | | 7/2012 | Milijasevic | |
| 2012/0316492 | A1 | | 12/2012 | Chappel | |
| 2013/0046253 | A1 | | 2/2013 | Yavorsky et al. | |
| 2014/0166528 | A1 | | 6/2014 | Bianchi | |
| 2015/0290389 | A1 | * | 10/2015 | Nessel | F04B 3/00 |
| | | | | | 604/152 |
| 2015/0346732 | A1 | | 12/2015 | Chappel | |
| 2016/0175515 | A1 | | 6/2016 | Mccullough | |
| 2016/0206811 | A1 | | 7/2016 | Shih et al. | |
| 2016/0213851 | A1 | * | 7/2016 | Weibel | A61B 5/14532 |
| 2016/0271324 | A1 | | 9/2016 | Chappel et al. | |

FOREIGN PATENT DOCUMENTS

| JP | H10-057487 A | 3/1998 |
|---|---|---|
| JP | 2009-531111 A | 9/2009 |
| JP | 2012-000470 A | 1/2012 |
| WO | WO 2005044343 A1 | 5/2005 |
| WO | WO 2008021252 A1 | 2/2008 |
| WO | WO 2009017487 A1 | 2/2009 |
| WO | WO 2010008675 A1 | 1/2010 |
| WO | 2010020891 A1 | 2/2010 |
| WO | WO 2010020891 | 2/2010 |
| WO | WO 2011011814 | 2/2011 |
| WO | 2011098867 A1 | 8/2011 |
| WO | 2011098946 A1 | 8/2011 |
| WO | WO 2011098867 | 8/2011 |
| WO | WO 2011098946 | 8/2011 |
| WO | WO 2014090745 | 6/2014 |
| WO | 2014108860 A1 | 7/2014 |
| WO | WO 2014108860 | 7/2014 |
| WO | 2020012308 A1 | 1/2020 |
| WO | WO 2020012308 | 1/2020 |
| WO | WO2020075042 | 4/2020 |
| WO | 2020129002 A1 | 6/2020 |
| WO | WO 2020129002 | 6/2020 |

OTHER PUBLICATIONS

Office Action issued in Japanese Patent Application No. 2020-543070 dated Jun. 20, 2023.
European Search Opinion dated Jan. 7, 2019 for Application No. EP18182850.0.
European Search Report dated Jan. 7, 2019 for Application No. EP18182850.0.
International Search Report dated Apr. 23, 2019 for Application No. PCT/IB2019/051237.
International Search Report dated Mar. 19, 2020 for Application No. PCT/IB2019/061189.
International Search Report dated Oct. 23, 2019 for Application No. PCT/IB2019/055742.
Written Opinion of the ISA dated Apr. 23, 2019 for Application No. PCT/IB2019/051237.
Written Opinion of the ISA dated Mar. 19, 2020 for Application No. PCT/IB2019/061189.
Written Opinion of the ISA dated Oct. 23, 2019 for Application No. PCT/IB2019/055742.
Non-Final Office Action, issued in U.S. Appl. No. 17/056,769 dated Jan. 19, 2024.

* cited by examiner

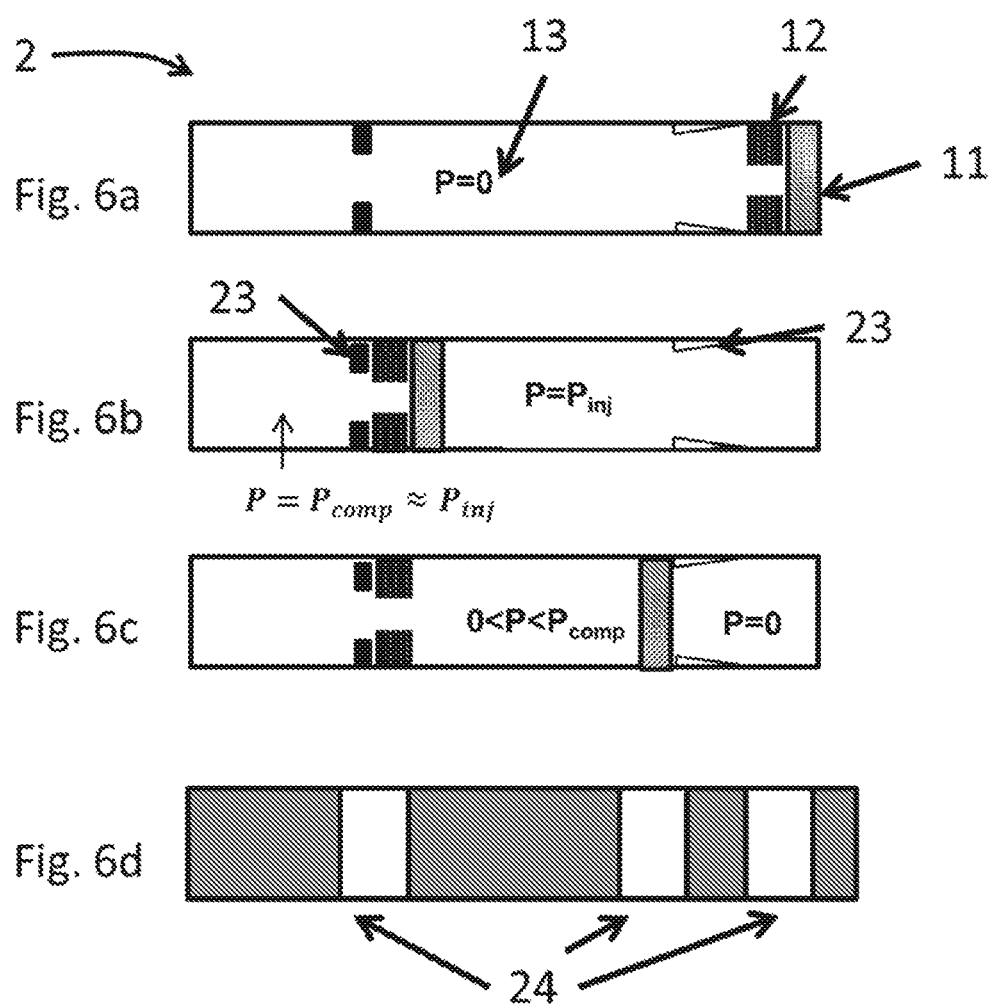

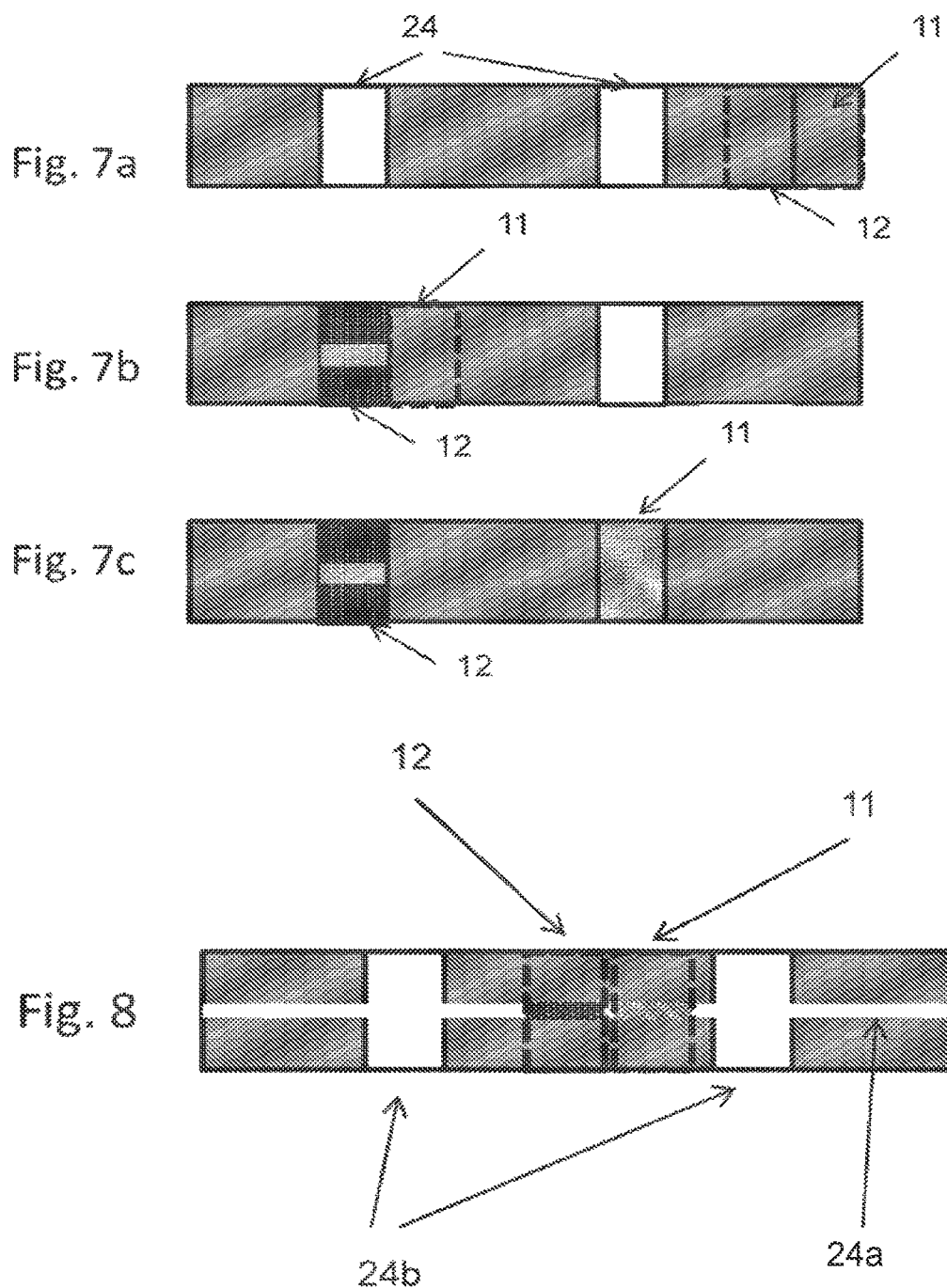

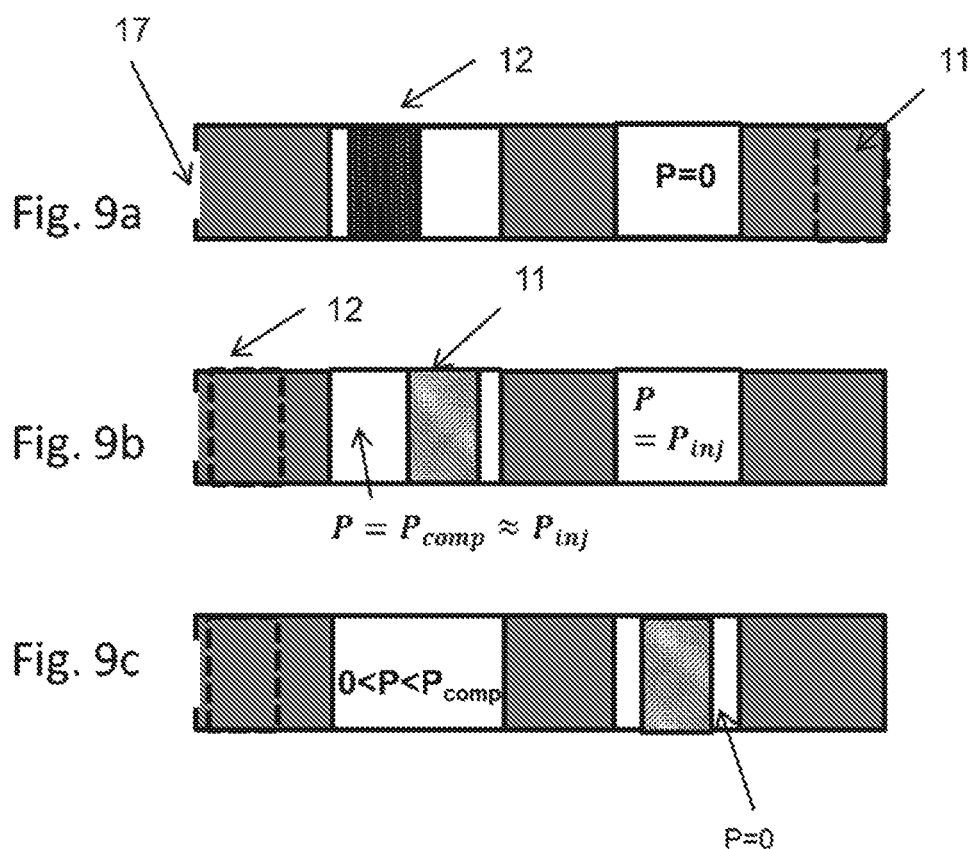

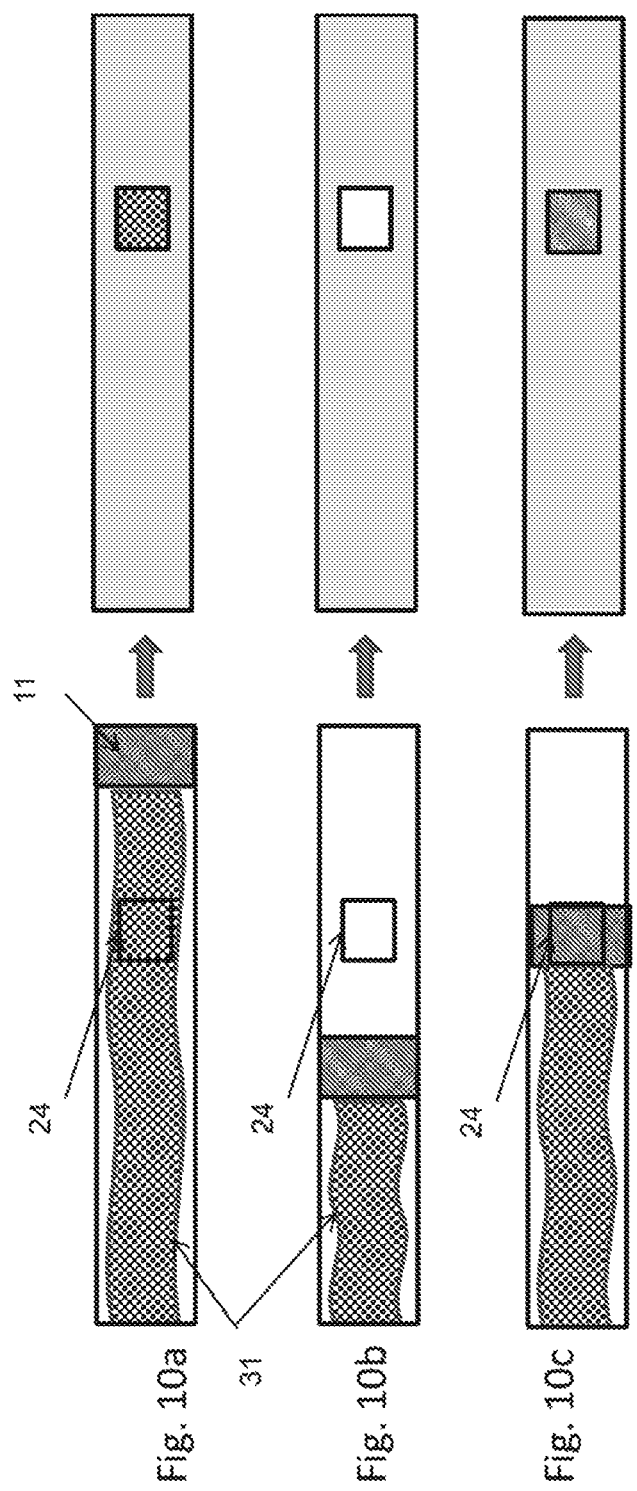

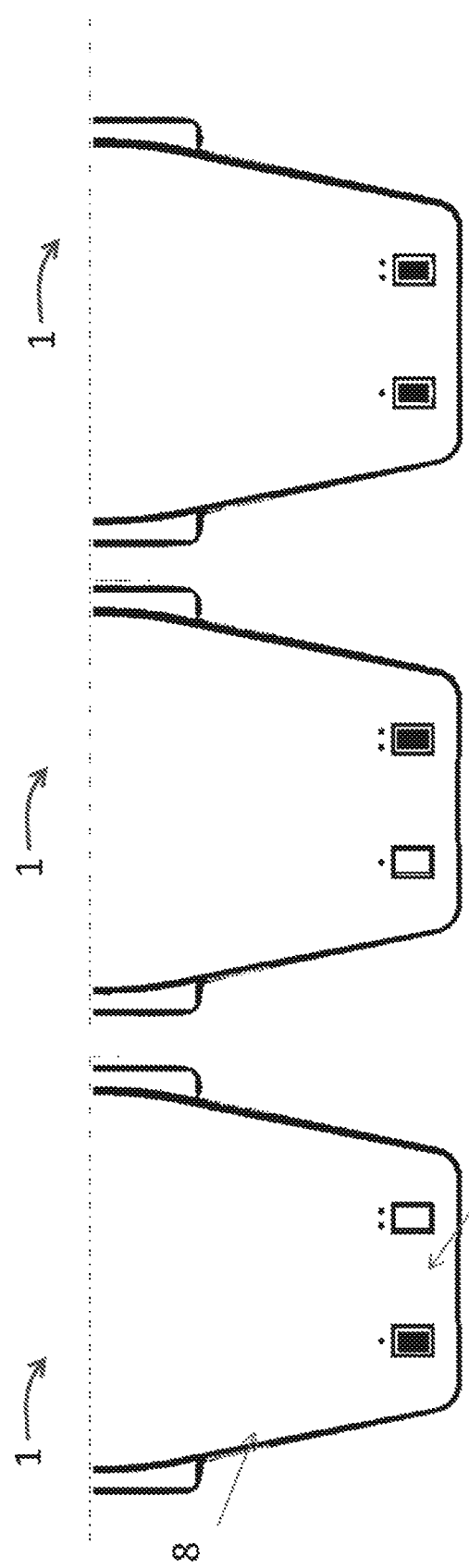

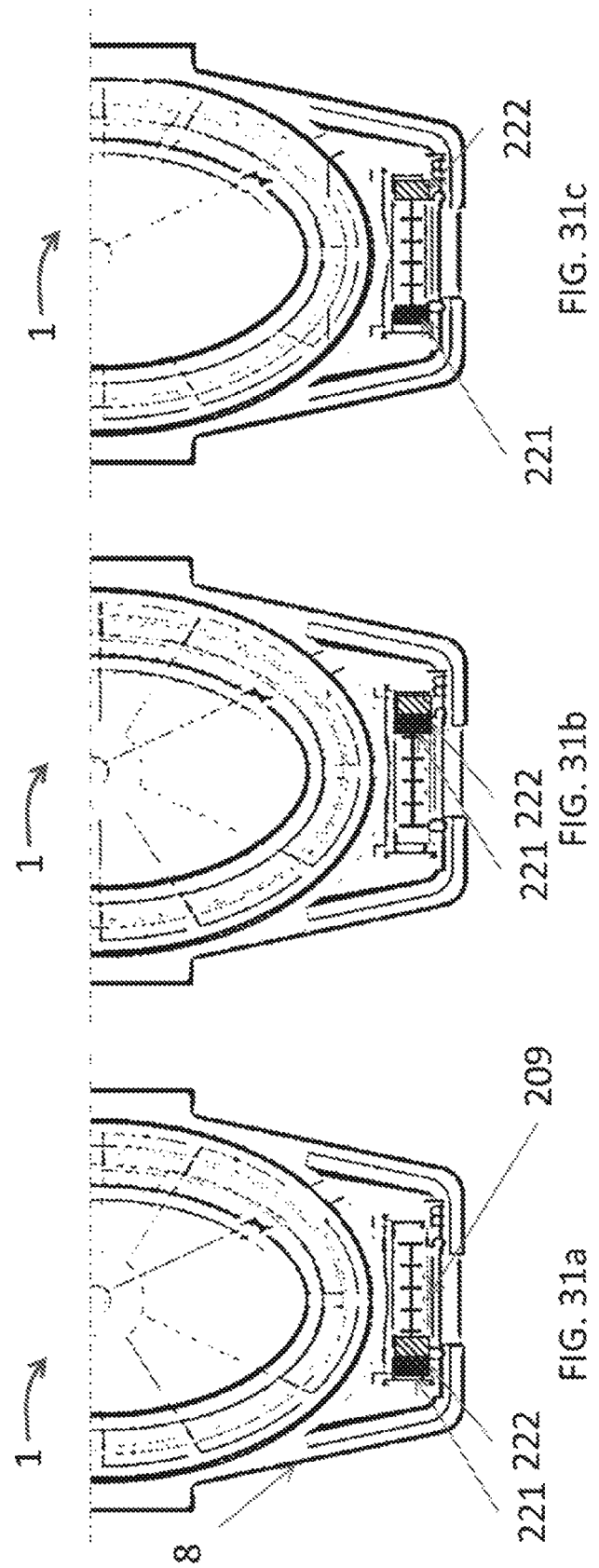

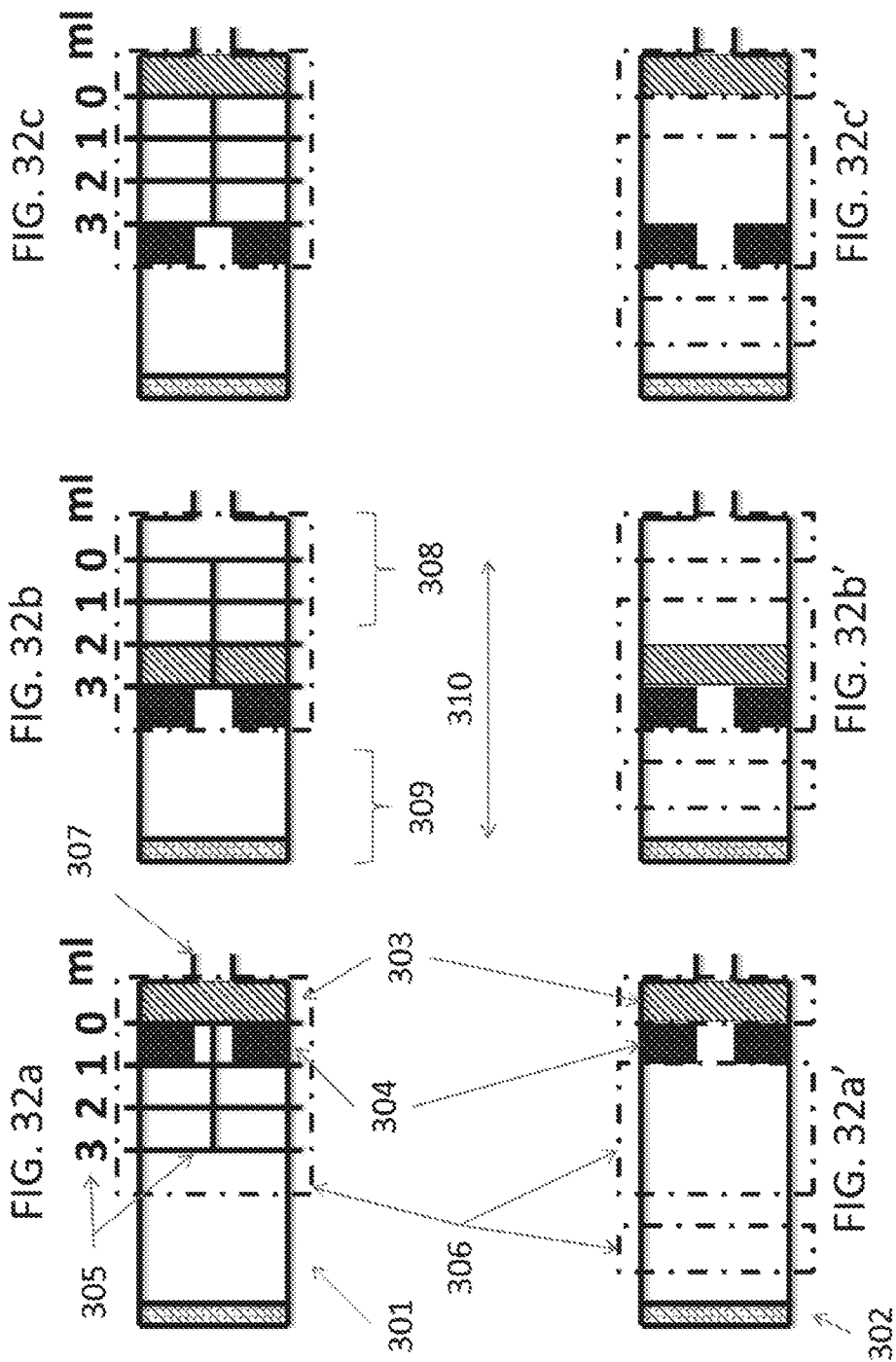

311

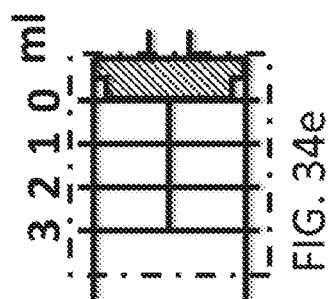
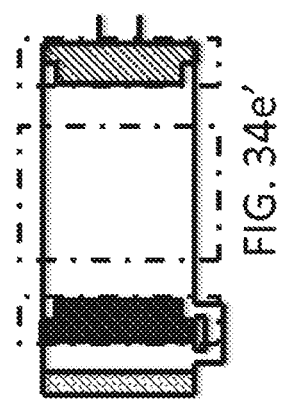
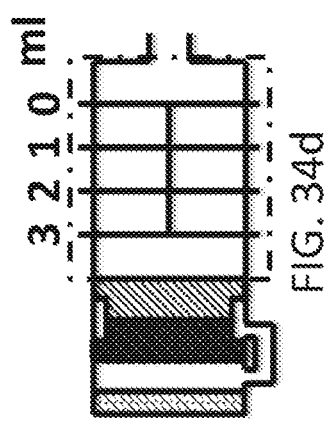
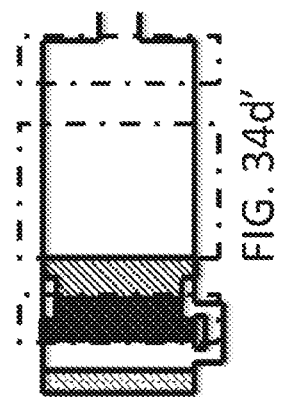

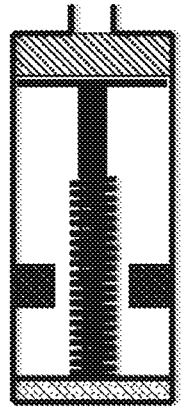
FIG. 36a
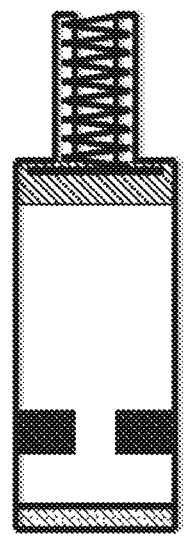
FIG. 36d
FIG. 36b
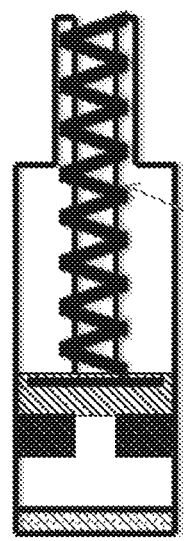
FIG. 36e
FIG. 36c
FIG. 36f

STATUS INDICATOR OF A DRUG DELIVERY SYSTEM

CROSS REFERENCE TO RELATED APPLICATIONS

The present application is a United States national stage application of International patent application PCT/IB2019/051237 filed on Feb. 15, 2019 designating the United States, and claims foreign priority to European Patent Application Numbers EP18157250.4 filed on Feb. 16, 2018, EP18182850.0 filed on Jul. 11, 2018, EP18215745.3 filed on Dec. 21, 2018, EP19151323.3 filed on Jan. 11, 2019, EP19151324.1 filed on Jan. 11, 2019, EP19151325.8 filed on Jan. 11, 2019, and EP19155800.6 filed on Feb. 6, 2019, the contents of all seven (7) documents being herewith incorporated by reference in their entirety.

FIELD OF INVENTION

The present document discloses an indicator device configured to provide information to a user for example a status of a delivery system such as a drug delivery system which may be configured to infuse a single bolus. The present document further discloses an example of a delivery system which may be used with an indicating device and other potential features and devices.

STATE OF THE ART

New therapies developed by pharmaceutical companies require a new generation of delivery system. Said new generation of delivery system has to allow the infusion of a determined amount of fluid to a patient over a time period. Some therapies may require infusing the entire content of the reservoir into a single bolus.

Preferentially, the delivery system can only be used once thus after used the delivery system may be discarded. Such system may be cheap, user-friendly and may not comprise any electronic component.

This document describes various embodiments such as a smart and cheap indicator device for a delivery system, a delivery system and other embodiments or features, for example a valve device, a filling indicator device, a failure indicator device.

GENERAL DESCRIPTION

The present document discloses an indicator device which comprises one or more movable element (for example a single plunger, two plungers or other) configured to indicate at least one of a status of the infusion, a filling level and a failure. The present document further discloses a valve allowing the occlusion of a fluid pathway and a delivery system.

One of the goals of disclosed embodiments is to present directly or indirectly, to a user, at least one information (preferentially at least two, more preferentially three) related to the current status of the delivery system. Preferentially, the device is configured to provide a signal (for example a visual signal, a discrete signal, . . . ) indicating at least one of following states or information: before infusion, during infusion, at the end of the infusion, before reservoir filling, during reservoir filling, at the end of the reservoir filling, filling level, fluid flow condition, ready to fill the reservoir, ready to infuse, infusion in progress, fill in progress, failure, and leakage. The indicator device comprises at least one movable element (for example a plunger) configured to reach determined positions in response to the status of the delivery system.

A first aspect of the disclosure relates to an indicator device for indicating the status of bolus delivery to a patient via a medical system. The medical system (such as a delivery system) preferentially comprises a reservoir with an internal compartment storing a solution to be delivered and a transcutaneous device. The indicator device may comprise:
 a body which includes or surrounds an internal cavity having:
  a fluid port adapted to be coupled to at least one of the reservoir and the transcutaneous device,
  a first end, and
  a second end, wherein the first end and the second end defines a main axis, and
 a first movable element and a second movable element disposed into the internal cavity and configured to move relatively to the body through the internal cavity in a parallel direction to the main axis The first movable element is preferentially in pressure communication with at least one of the internal compartment and the transcutaneous device. The indicator device is preferentially configured to provide an indication relative to at least two states of the following list: before infusion, during infusion, and at the end of the infusion by means of distinct positions of the first and second movable elements within the internal cavity.

The indicator device may further comprise a position indicator window disposed on an exterior surface of the indicator device and configured to provide an external visual indication of the position of at least one of the first and second moveable elements.

The fluid port may be in fluid communication with at least one of the internal compartment of the reservoir and the transcutaneous device.

The internal cavity may comprise a first variable volume, a second variable volume, and a third variable volume defined by the internal wall of the internal cavity and at least of the first movable element and the second movable element. The first variable volume may be in fluid communication with the fluid port. The first movable element may tightly separate the first variable volume and the second variable volume. The second movable element may comprise a fluid pathway (for example a through hole) configured to provide a fluid communication between the second variable volume and the third variable volume.

The first movable element may be configured to push the second movable element from a first position to a second position.

The first movable element may be configured to perform a back-and-forth motion. In some embodiments, the first movable element may be configured to perform a back-and-forth motion while the second movable element perform a simple motion caused by the forth motion of the first movable element. The indicator device may further comprise a biasing means configured to induce the back motion of at least of the first movable element and the second movable element.

The indicator device may further comprise a vent configured to provide a pressure equilibration of the third variable volume with an external environment. In some embodiment, where the reservoir is pressurized by a fluid (for example a pressurized gas), the third variable volume may be in fluid or pressure communication with pressurized fluid and may induce the back motion of the first movable element.

A second aspect of the disclosure relates to a medical system adapted to deliver a solution to a patient, which may include:
- An indicator device as described in this document,
- A reservoir which may comprise a movable wall,
- A transcutaneous device in fluid communication with the patient,
- A fluid pathway extending from the internal compartment of the reservoir to the transcutaneous device,
- A housing which surrounds a cavity of the medical system in which the movable wall may move, and
- A (at least one) vent device configured to provide a pressure equilibration of the system cavity with an external environment.

The indicator device and/or the medical system may further comprise a valve device configured to occlude a part of the fluid pathway. The first movable element of the indicator device may be configured to occlude a part of the fluid pathway when the first movable element is in a determined position (for example initial position).

The medical system may further comprise a removably occluding device configured to occlude the (at least one or all) vent device at least during a filling process of the reservoir or a storing period.

The medical system may further comprise a pressurized reservoir in pressure communication with the movable wall of the reservoir. The indicator device may comprise an additional cavity in fluid and/or pressure communication with the pressurized reservoir. The indicator device may comprise an additional movable element configured to move into the additional cavity for example along a direction parallel to a main axis of the indicator device. The additional part of the indicator device may provide an indication relates to a state of the pressurized reservoir, such as a failure or a leakage by means of distinct position of the additional movable element into the additional cavity.

The cavity and the additional cavity may be tightly separated to each other. In some embodiments a fluid communication may be opened between both cavities and the fluid pressurized of the pressurized reservoir may induce a back motion of at least one movable element (for example the first movable element described above).

A third aspect of the disclosure relates to an indicator device for indicating the status of a delivery system. The delivery system preferentially comprises a first reservoir with a first internal compartment for storing a first fluid. The indicator device may comprise:
- a body which includes an internal cavity having a fluid port in pressure communication with the first internal compartment, the internal cavity may further comprise a first end and a second end defining a main axis,
- at least one movable element disposed into the cavity and configured to move relatively to the internal cavity in a parallel direction to the main axis, the at least one movable element may be configured to move in response to pressure of the first fluid stored in the first internal compartment and the at least one movable element may comprise at least two distinct positions: a first position and a second position; and
- a position indicator window disposed in the vicinity of at least one of the first position and the second position, the position indicator window may be arranged on an exterior surface (or side) of the indicator device (or of the delivery system) such that the position indicator window provides a visual indication of the position of the at least one moveable element.

The indicator device may indicate at least one state of the delivery system by means of the distinct positions of the at least one movable element.

The indicator device may provide an indication relative to at least one of the following states:
- before infusion,
- during infusion,
- at the end of the infusion,
- before reservoir filling,
- during reservoir filling,
- at the end of the reservoir filling,
- ready to infuse,
- ready to fill,
- infusion in progress,
- fill in progress,
- a failure, and
- a leakage.

The at least one moveable element may be in pressure communication with the first fluid stored into the first internal compartment.

The at least one moveable element may comprise at least one of a first plunger and a second plunger.

The fluid port may be in fluid communication with the first fluid stored into the first internal compartment.

The first fluid stored into the first internal compartment may be intended to be delivered to a patient. In another embodiment, the first fluid stored into the first internal compartment is intended to pressurize a second reservoir having a second internal compartment storing a second fluid intended to be delivered to a patient.

A fourth aspect of the disclosure relates to a delivery system comprising a housing surrounding a system cavity (for example an internal cavity of the delivery system which may be at least defined by the housing), a vent device and an indicator device (as described in this document). The first reservoir preferentially comprises a movable wall configured to vary the first internal compartment of the first reservoir.

The movable membrane may be configured to move at least partially into the system cavity. The vent device preferentially provides an equilibration pressure of the system cavity with an external environment of the system.

The system may further comprise an occluding device (which may be removed) configured to occlude the vent device during at least one of a filling of the first reservoir and a storage period before using.

A fifth aspect of the disclosure relates to an indicator device for indicating an infusion status of a medical device adapted to deliver a solution to a patient. The indicator device may include a body, an elongated cavity arranged into the body and having a first end and a second end (which defines a main axis), and at least two plungers (a first plunger and a second plunger; optionally an additional plunger) configured to move relative to the elongated cavity (for example along a parallel direction of the main axis). Preferentially, the first plunger and the second plunger are arranged into the elongated cavity in such a manner to define at least one variable volume, for example three variable volumes:
- a first variable volume formed between the first end of the elongated cavity and the first plunger,
- a second variable volume formed between the first plunger and the second plunger, and
- a third variable volume formed between the second plunger and the second end of the elongated cavity.

The first plunger may be configured to move depending on the pressure of the solution intended to be delivered.

The first plunger may provide a fluid-tight wall between the first variable volume and the second variable volume.

The first variable volume, the second variable volume and the third variable volume may comprise a fluid such as a liquid or a gas for example air or compressible fluid. The first variable volume may be configured to receive a volume fraction of the solution which may be expelled from the first variable volume at the end of the infusion.

The first plunger may perform forward and backward motion.

The first plunger (or the first variable volume) may be in pressure communication with the solution intended to be infused to the patient and a pressure gradient or a pressure variation of this solution may cause or allow the first plunger motion.

For example, the first plunger (or the first variable volume) may be in pressure communication with a reservoir storing the solution intended to be infused. This reservoir may be a pressurized reservoir. The medical device may comprise the reservoir and a housing in which the reservoir is arranged.

The first end of the cavity may comprise a fluid port in fluid communication with the solution intended to be delivered. For example, the fluid port may be in fluid communication with the reservoir storing the solution or with the fluid pathway between the internal compartment of the reservoir and an outlet of the medical device.

The second plunger may move depending on the first plunger. For example, the first plunger may push the second plunger from a position to a determined position which may be visible or hidden to the user. In this purpose, the indicator device may comprise one or more windows in order to render visible at least one of the first plunger and the second plunger in determined position(s).

The second plunger may comprise a through hole configured to provide a fluid communication between the second variable volume and the third variable volume.

The indicator device may allow a discrete visual signal indicating a fluid flow condition depending on the position of at least one of the first plunger and the second plunger. Depending on the position of the plungers, the plungers may be visible or hidden to the user, in order to indicate a status of the medical device such as ready to inject, infusion on-going or end of infusion.

The elongated cavity may further comprise a mechanical stop (also called stop member) arranged between the first end and the second end in order to maintain at least one of the first plunger and the second plunger in a determined position.

The second end may comprise a vent in order to provide a pressure equilibration of the third variable volume with the outside environment.

The indicator device may further comprise a biasing device arranged between the first plunger and the second plunger.

A sixth aspect of the disclosure relates to an indicator device for indicating an infusion status of a medical device adapted to deliver a solution to a patient. The indicator device may include a body, an elongated cavity arranged into the body and having a first end and a second end, and a first plunger configured to move relative to the elongated cavity. Preferentially the first plunger is arranged into the elongated cavity and may be configured to have at least one (stable) position. More preferentially, the first plunger may be configured to have at least two distinct positions, for example three distinct positions: a first initial position, a second position, and a third position.

The first plunger may be configured to move depending on the pressure of the solution intended to be delivered.

The first plunger may perform forward and backward motion.

The first plunger may provide a fluid-tight wall between a first variable volume and a second variable volume. The first variable volume may be defined between the first end of the cavity and the first plunger and the second variable volume may be defined between the first plunger and another end of the cavity, for example an opposite end of the first end, which may be the second end.

The first plunger (or the first variable volume) may be in pressure communication with the solution intended to be infused to the patient and a pressure gradient or a pressure variation of this solution may cause or allow the first plunger to move.

For example, the first plunger (or the first variable volume) may be in pressure communication with a reservoir storing the solution intended to be infused. This reservoir may be a pressurized reservoir. The medical device may comprise the reservoir and a housing in which the reservoir is arranged.

The first end of the cavity may comprise a fluid port in fluid communication with the solution intended to be delivered. For example, the fluid port may be in fluid communication with the reservoir storing the solution or with the fluid pathway between the internal compartment of the reservoir and an outlet of the medical device.

The indicator device may allow a discrete visual signal indicating a fluid flow condition depending on the position of the first plunger. Depending on the position of the first plunger, the plunger may be visible or hidden to the user, in order to indicate a status of the medical device such as ready to inject, infusion on-going or end of infusion. In this purpose, the indicator device may comprise one or more windows in order to render visible the first plunger in at least one of the first initial position, the second position and the third position.

The elongated cavity may further comprise a mechanical stop (also called stop member) arranged between the first end and the second end in order to maintain the first plunger in a determined position (the first initial position, the second initial position, or the third position).

The second end may comprise a vent in order to provide a pressure equilibration of the second variable volume with the outside environment.

The indicator device may further comprise a biasing device arranged between the first plunger and the second end of the cavity.

The indicator may comprise a second plunger which may be arranged into the cavity between the first plunger and the second end of the cavity. The second plunger may move depending on the first plunger (for example depending on the plunger motion according to a determined way/direction). For example, the first plunger may push the second plunger from a position to a determined position which may be visible or hidden to the user. For this purpose, the indicator device may comprise one or more windows in order to render visible at least one of the first plunger and the second plunger in determined position(s).

The second plunger may comprise a through hole configured to provide a fluid communication between the volume defined between the first plunger and the second plunger and the other volume defined between the second plunger and the second end.

A seventh aspect of the disclosure relates to an indicator device indicating an infusion status of a medical device adapted to deliver a solution to a patient. The indicator device may include:
- a body having a window and an elongated cavity arranged into the body and having a first end and a second end,
- a first plunger configured to provide a visual signal through the window and to move relative to the elongated cavity, and
- a compressible visual element configured to provide a visual signal through the window.

Preferentially, the first plunger and the compressible visual element are arranged into the elongated cavity. The compressible visual element may be configured to be compressed into the cavity between the second end of the cavity and the first plunger when the plunger moves toward the second end of the cavity.

The first plunger may be configured to move depending on the pressure of the solution intended to be delivered.

The first plunger may perform forward and backward motion and the compressible visual element may be used as a biasing means which exerts an opposite force to the solution pressure against the first plunger.

The first plunger (or the first variable volume) may be in pressure communication with the solution intended to be infused to the patient and a pressure gradient or a pressure variation of this solution may cause or allow the first plunger motion.

For example, the first plunger (or the first variable volume) may be in pressure communication with a reservoir storing the solution intended to be infused. This reservoir may be a pressurized reservoir. The medical device may comprise the reservoir and a housing in which the reservoir is arranged.

The first end of the cavity may comprise a fluid port in fluid communication with the solution intended to be delivered. For example, the fluid port may be in fluid communication with the reservoir storing the solution or with the fluid pathway between the internal compartment of the reservoir and an outlet of the medical device.

The indicator device may allow a discrete visual signal indicating a fluid flow condition depending on the position of at least one of the first plunger and the compressible visual element. Depending on the position of the plunger and the compressible visual element, the plunger and/or the compressible visual element may be visible or hidden to the user, in order to indicate a status of the medical device such as ready to inject, infusion on-going or end of infusion. When the medical device is in a first status, the window may allow seeing the compressible visual element, for example the user can see an orange color indicating that the medical device is ready to inject. When the medical device is in a second status, the window may allow seeing a wall of the cavity, for example the user can see a green color indicating that the solution is flowing to the patient. When the medical device is in a third status, the window may allow seeing the plunger, for example the user can see a blue color indicating that the infusion is ended.

The elongated cavity may further comprise a mechanical stop arranged between the first end and the second end in order to maintain at least one of the first plunger and the compressible visual element at a determined position.

The second end may comprise a vent in order to provide a pressure equilibration (of the volume between the second end and an end of the compressible visual element or of the first plunger) with the outside environment.

The indicator device may further comprise a biasing device. The biasing means may be a gas trapped between the first plunger and the second end or the compressible visual element.

The compressible visual element may be a plunger having an elongated body which is configured to fold when it is compressed.

An eighth aspect of the disclosure relates to a medical device adapted to deliver a solution to a patient. The medical device may include an indicator device, a pressurized reservoir to store the solution, an outlet port in fluid communication with the patient, and a fluid pathway from the interior of the pressurized reservoir to the outlet port.

The indicator device may be one of the disclosed indicator device. For example, the indicator device may comprise an elongated cavity arranged into the medical device and having a first end and a second end, and a first plunger configured to move relative to the elongated cavity.

Preferentially, the indicator device is in pressure communication with the fluid pathway.

The first plunger may be configured to move depending on the pressure of the solution stored in the pressurized reservoir or the fluid present into a part of the fluid pathway.

The first plunger may perform forward and backward motion.

The first plunger may provide a fluid-tight wall between a first variable volume and a second variable volume. The first variable volume may be defined between the first end of the cavity and the first plunger and the second variable volume may be defined between the first plunger and another end of the cavity, for example an opposite end of the first end, which may be the second end. The indicator device may comprises an additional plunger arranged into the cavity for example between the first plunger and the second end and may divide the second variable volume into a second variable volume and a third variable volume.

The first plunger (or the first variable volume) may be in pressure communication with the solution initially stored into the pressurized reservoir or present into a part of the fluid pathway. A pressure gradient or a pressure variation of this solution may cause or allow the first plunger motion.

Preferentially, the medical device comprises a housing in which may be arranged a part of the indicator device, a part of the reservoir, and a part of the fluid pathway.

The indicator device may allow a discrete visual signal indicating a fluid flow condition depending on the position of the plunger(s). Depending on the position of the plunger(s), the plunger(s) may be visible or hidden to the user, in order to indicate a status of the medical device such as ready to inject, infusion on-going or end of infusion. For this purpose, the indicator device and/or the medical device may comprise one or more windows in order to render visible the plunger(s) in at least one position.

One of the goals of disclosed embodiments is to prevent any free flow before the activation of the delivery system, for example when the user fills the reservoir.

A ninth aspect of the disclosure provides a valve device arranged into a fluid pathway as described above. The valve device may be configured in order to allow the solution flow to the outlet when the pressurized reservoir or the solution pressure reaches a predetermined threshold.

A tenth aspect of the disclosure relates an indicator device configured to provide an indication relates to at least one of a filling of a drug reservoir and a status of the drug delivery. The indicator device preferentially comprises a body having a cavity. The cavity includes a first end and a second end which define a main axis. The indicator device comprises an inlet port in pressure communication with an internal compartment of the drug reservoir. The indicator device further comprises at least one movable element (preferentially a first movable element and a second movable element) and at least one visual indicator arranged in vicinity to a possible position of the movable element. The indicator device provides an indication by means of the visual indicator and the distinct position of the movable element within the cavity.

An eleventh aspect of the disclosure relates to an indicator device configured to provide an indication of the states of a pressured reservoir. The pressurized reservoir may be configured to apply a pressure on a drug reservoir (for example on a movable wall of a drug reservoir). The indicator device may comprise a body having a first cavity with a first end and a second end defining a main axis. The indicator device preferentially comprises a movable element (for example a plunger) configured to move in the cavity along a parallel direction of the main axis. The indicator device may further comprise a fluid port which may be in fluid communication with the pressurized reservoir and the movable element may be in pressure communication with the pressurized fluid stored in the pressurized reservoir. The indicator device is preferentially configured to indicate a failure of the pressurized reservoir (for example a leakage) by means of position of the movable element within the first cavity.

In some embodiments the indicator device may further comprise a second cavity in which one or more additional movable element is configured to provide an indication relates to at least one of a filling of the drug reservoir and a status of the delivery as described in this document.

Preferentially, the device does not need any power source such as battery or electronic device connected to the indicator device or the valve device. The (linear) movement is due to the pressure of the solution in the drug reservoir and/or in the fluid pathway (between the reservoir and the outlet device).

LIST OF FIGURES

The present disclosure will be better understood at the light of the following detailed description which contains non-limiting examples illustrated by the following figures.

Figure 5A:
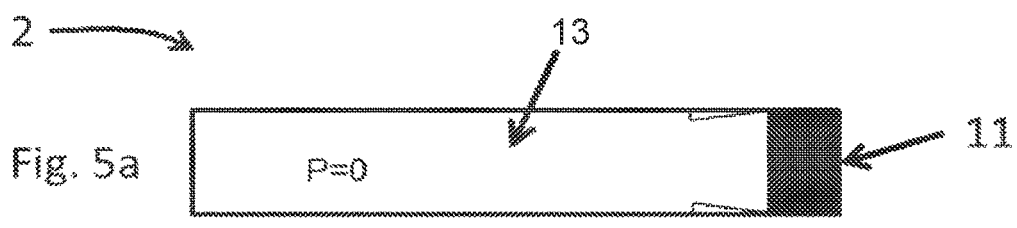
Figure 5B:
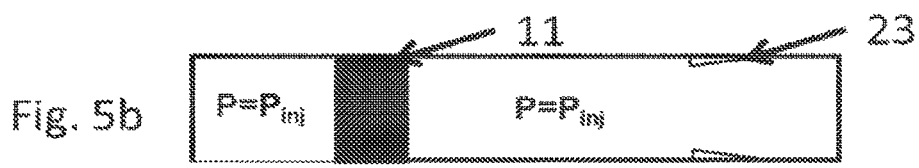
Figure 5C:
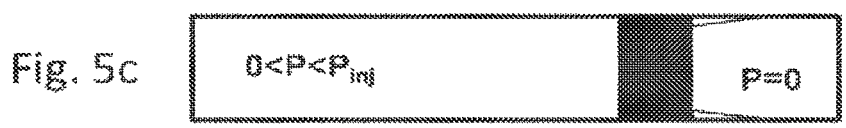
Figure 5D:
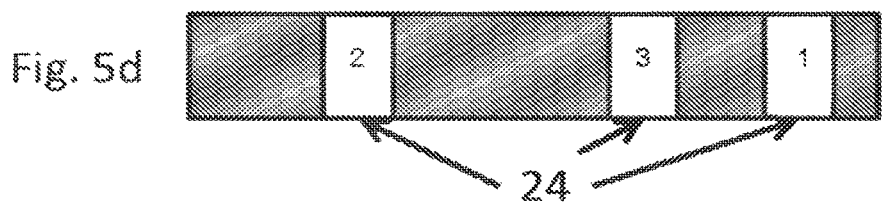

FIGS. 5a, b, c, and d show an embodiment wherein the indicator device comprises a single plunger having a mechanical stop (for example conical narrowing) which may be configured to allow the definition of three different plunger positions. The FIG. 5a shows a first position related to the status "ready to inject", the FIG. 5b shows a second position related to the status "infusion on-going", and FIG. 5c shows a third position related to the status "end of infusion". The FIG. 5d shows three windows placed in front of the infusion status indicator (or at least one) may be configured to allow the visualization of the plunger (bottom figure).

FIGS. 6a, b, c, and d show an embodiment wherein the indicator device comprises a first mechanical stop (left part of the cylinder) and a second mechanical stop (conical narrowing in the right part of the cylinder). The three well defined positions of the two plungers before injection (FIG. 6a), during injection (FIG. 6b) and after injection (FIG. 6c) are shown. One or more windows may be arranged in front of the infusion status indicator to allow the visualization of the plungers (FIG. 6d).

FIGS. 7a, b, and c show an embodiment wherein the indicator device comprises two plunger and two distinct windows. The second plunger may be red while the first plunger may be green. Before infusion no plunger is visible (FIG. 7a). During infusion the second plunger is visible through the window located on the left part of the cylinder (FIG. 7b). At the end of the infusion the first plunger becomes visible through the window located on the right part of the cylinder (FIG. 7c).

FIG. 8 shows an embodiment wherein the dual plunger infusion status indicator comprises two vertical windows as well as a horizontal one. The plungers are in an intermediate position just after activation. The hole of the second plunger is not represented here for sake of clarity. The horizontal window is here useful to determine that the infusion has been activated since the plungers are no longer at their initial locations and not visible through at least one of the vertical windows.

FIGS. 9a, b, and c show an embodiment wherein the indicator device comprises a vent device for example the cavity (the third variable volume) is open to air. Before infusion only the second plunger is visible (FIG. 9a). During infusion the second plunger moves towards the end of the cavity while the first plunger becomes visible in the left window (FIG. 9b). At the end of the infusion the first plunger becomes visible through the window located on the right part of the cylinder (FIG. 9c).

FIGS. 10a, b, and c show an example of an indicator device comprising a compressible visual element and a plunger.

Figure 11A:
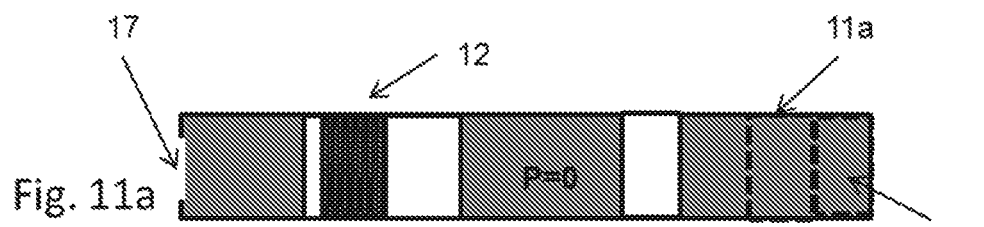
Figure 11B:
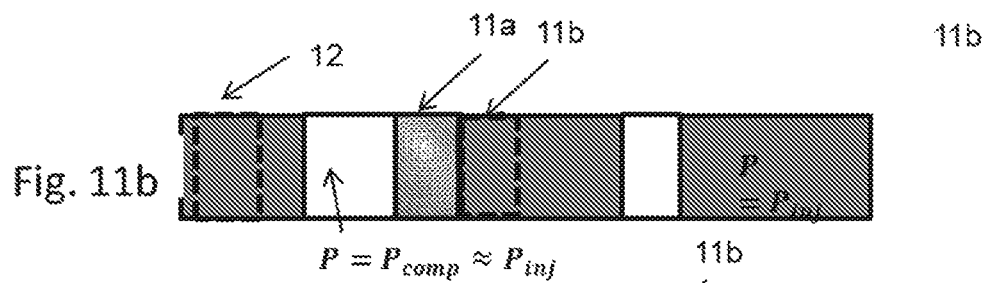
Figure 11C:
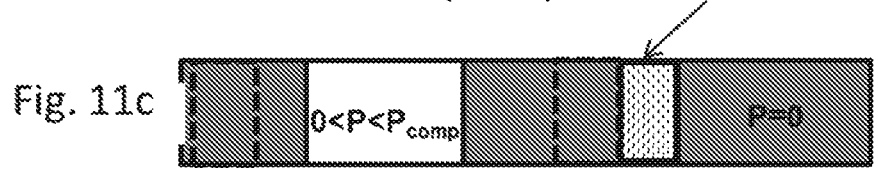

FIGS. 11a, b, and c show an embodiment wherein the indicator device comprises two windows and at least two plungers, and optionally wherein the cylinder is open to air. Before infusion only the second plunger is visible (FIG. 11a). During infusion the second plunger moves towards the end of the cylinder while a first part of the first plunger becomes visible in the left window (FIG. 11b). At the end of the infusion only a second part of the first plunger (or an additional plunger, for example a third plunger) is visible through the window located on the right part of the cylinder (FIG. 11c).

Figure 12A:
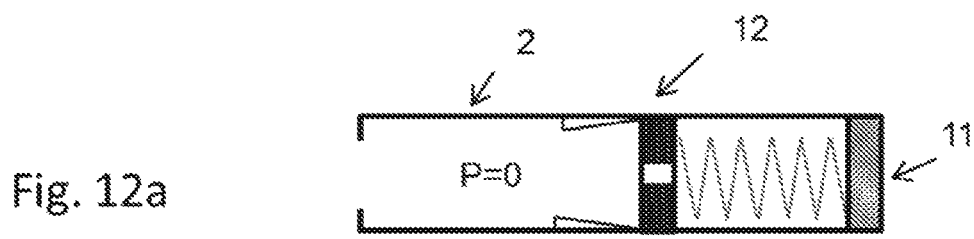
Figure 12B:
Figure 12C:
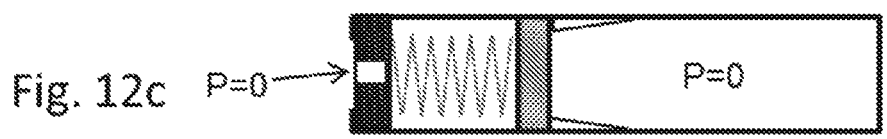
Figure 12D:

FIGS. 12a, b, c, and d show an embodiment wherein the indicator device comprises a biasing device (for example a spring) arranged between a first plunger and a second plunger. The three well defined positions of the two plungers before injection (FIG. 12a), during injection (FIG. 12b) and after injection (FIG. 12c) are shown. Windows placed in front of the infusion status indicator may be configured to allow the visualization of the plungers (FIG. 12d).

Figure 13A:
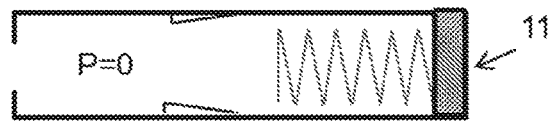
Figure 13B:
Figure 13C:
Figure 13D:
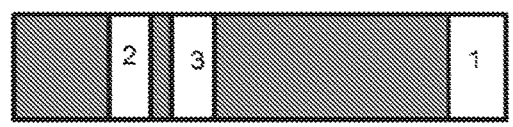

FIGS. 13a, b, c, and d show an embodiment wherein the indicator device comprises a biasing device (for example a spring) and a single plunger. The three well defined positions of the plunger before injection (FIG. 13a), during injection (FIG. 13b) and after injection are shown (FIG. 13c). Windows placed in front of the infusion status indicator may be configured to allow the visualization of the plungers (FIG. 13d).

Figure 14:
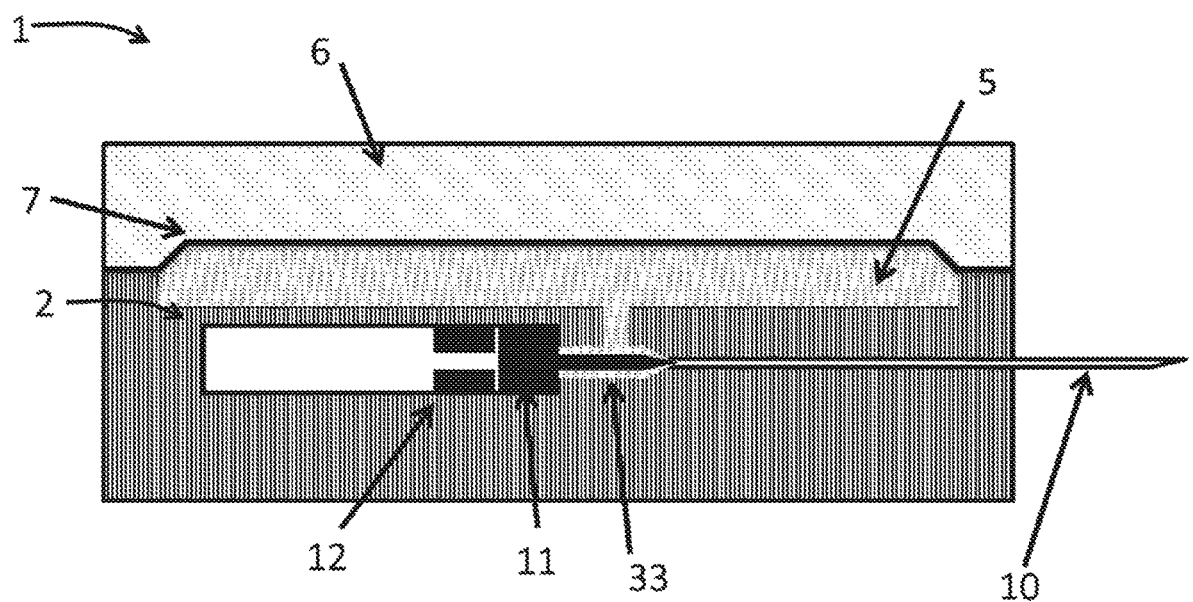

FIG. 14 shows an example of a drug delivery system before injection. Such drug delivery system may comprise a propellant reservoir (here liquefied gas), a drug reservoir tightly separated from the gas reservoir and an indicator device with a second plunger and a first plunger having a protrusion. The protrusion of the first plunger may be configured to block the flow as long as the pressure in the reservoir does not exceed a predefined value. The protrusion may be considered as a valve device of the fluid pathway.

Figure 15:
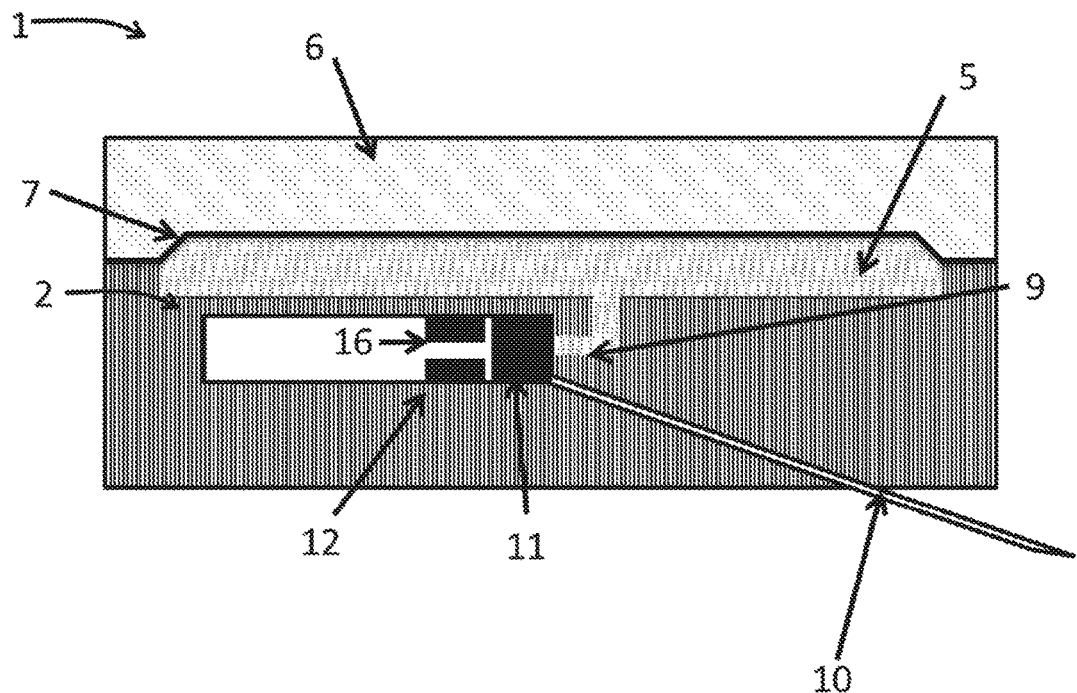

FIG. 15 shows an example of drug delivery system before injection comprising a propellant reservoir (here liquefied gas), a drug reservoir tightly separated from the gas reservoir, an indicator device having at least one plunger used as a valve device which blocks the flow as long as the pressure in the reservoir does not exceed a predefined value and a needle that is off-axis with the cylinder. In this example the first variable volume is a part of the fluid pathway or divides the fluid pathway in two distinct parts, a first part in fluid communication with the internal compartment of the reservoir and a second part in fluid communication with the outlet device (for example the needle).

Figure 16:
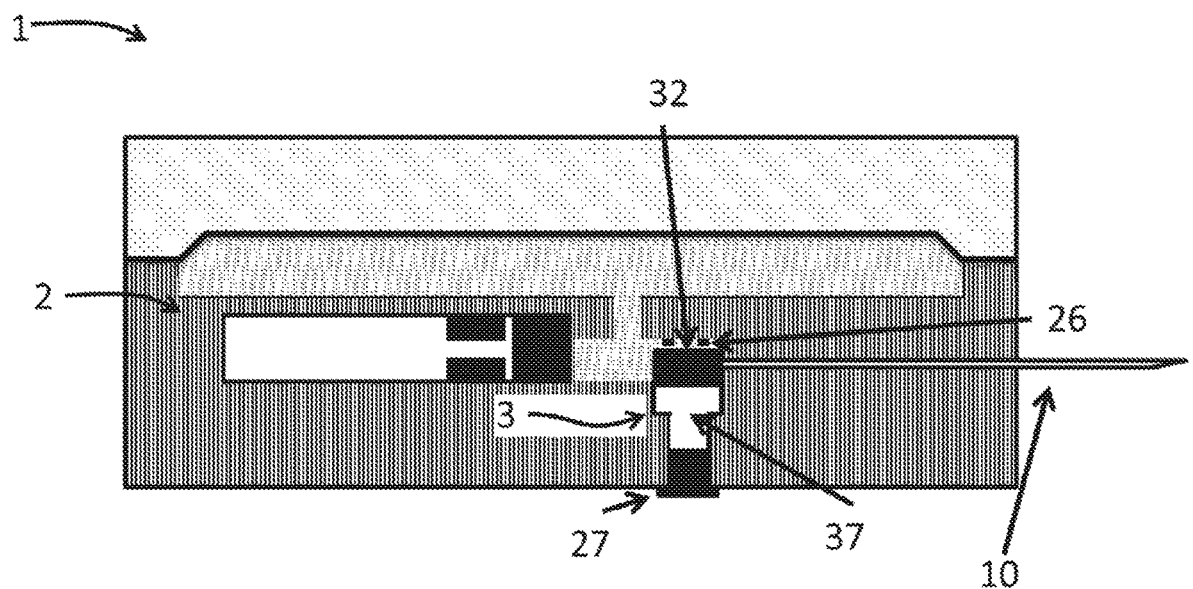

FIG. 16 shows an example of drug delivery system before injection, comprising a propellant reservoir (here liquefied gas), a drug reservoir tightly separated from the gas reservoir, a needle, a valve device, and an indicator device. The indicator device comprises a first and a second plunger. The valve device comprises a plunger adapted to move inside a cavity and a plug. The pressure of the drug applies onto the top surface of this plunger thanks to the presence of plunger stoppers. The user may have to remove the plug to allow the plunger of the valve device to open the fluid pathway. In the embodiment the indicator device is optional.

Figure 17:
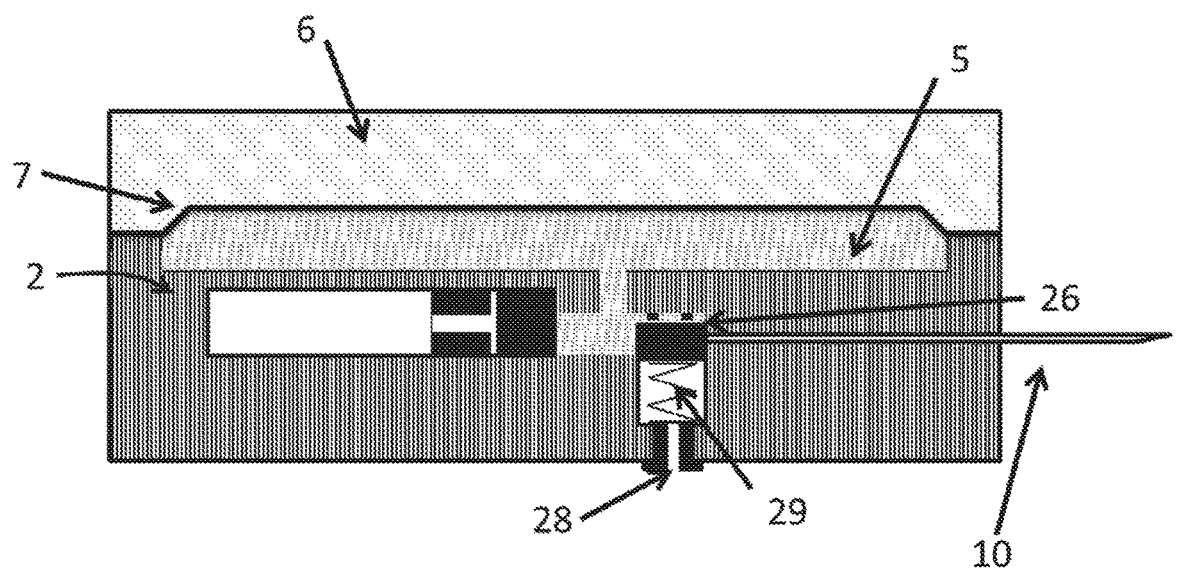

FIG. 17 shows an example of drug delivery system before injection, comprising a propellant reservoir (here liquefied gas), a drug reservoir tightly separated from the gas reservoir, a needle, an indicator device, and a valve device. The valve device may comprise a plunger inside a cavity in direct communication with the outlet device and a plug, said cavity comprising a spring and a vented and threaded adjustable plug. The pressure of the drug applies onto the top surface of the plunger thanks to the presence of plunger structuration. In the embodiment the indicator device is optional.

Figure 18:
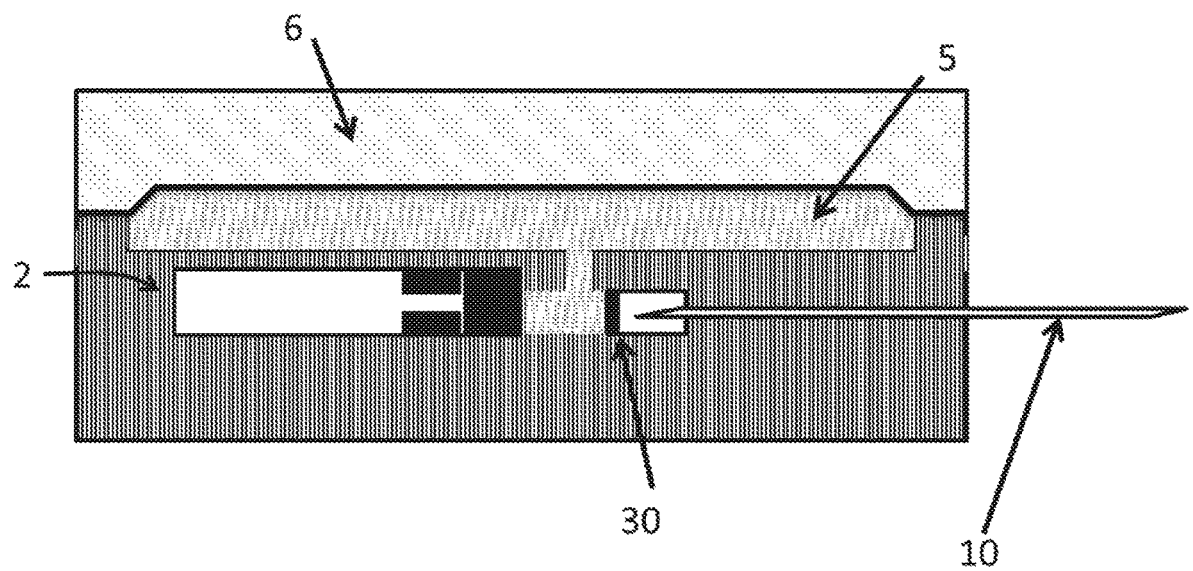

FIG. 18 shows an example of drug delivery system before injection, comprising a propellant reservoir (here liquefied gas), a drug reservoir tightly separated from the gas reservoir, an indicator device, and a valve device. The valve device comprises an elastomeric membrane used as crack valve and a double beveled needle (outlet device). In the embodiment the indicator device is optional.

Figure 19:
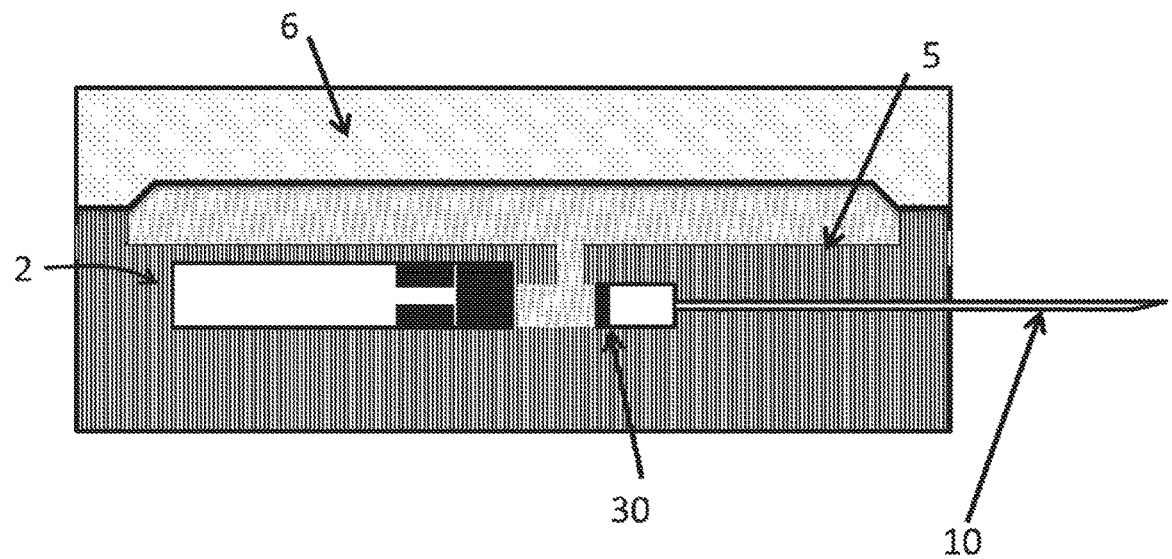

FIG. 19 shows an example of drug delivery system before injection, comprising a propellant reservoir (here liquefied gas), a drug reservoir tightly separated from the gas reservoir, an indicator device, and an elastomeric membrane used as crack valve and a needle. In the embodiment the indicator device is optional.

Figure 20:
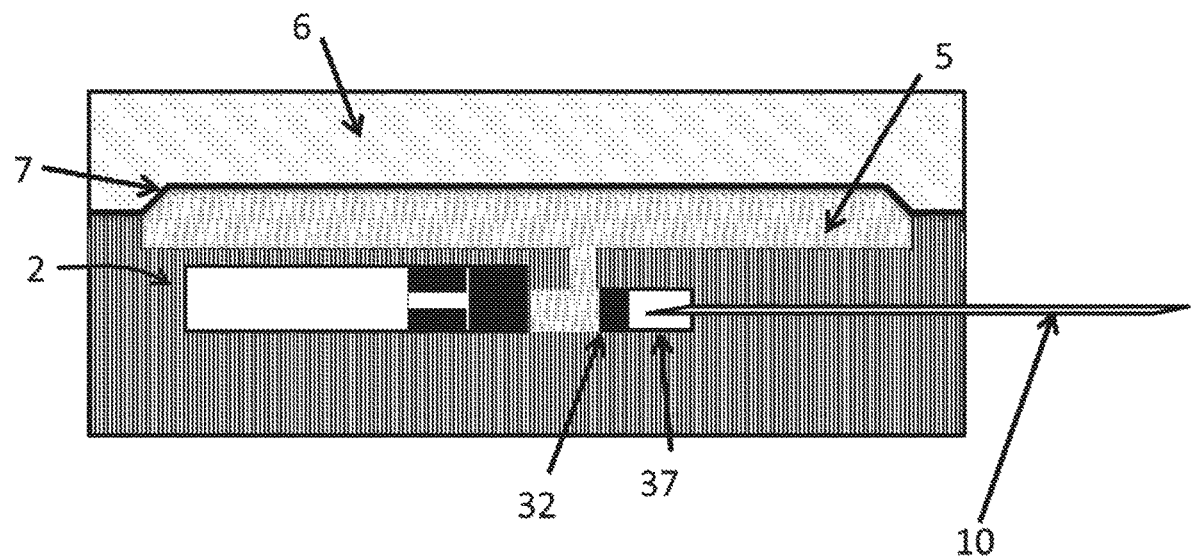

FIG. 20 shows an example of drug delivery system before injection, comprising a propellant reservoir (here liquefied gas), a drug reservoir tightly separated from the gas reservoir, a double beveled needle, an indicator device, and a valve device having a cylinder and a plunger being used as crack valve. In the embodiment the indicator device is optional. The plunger of the valve device is configured to move through the cylinder.

Figure 21:
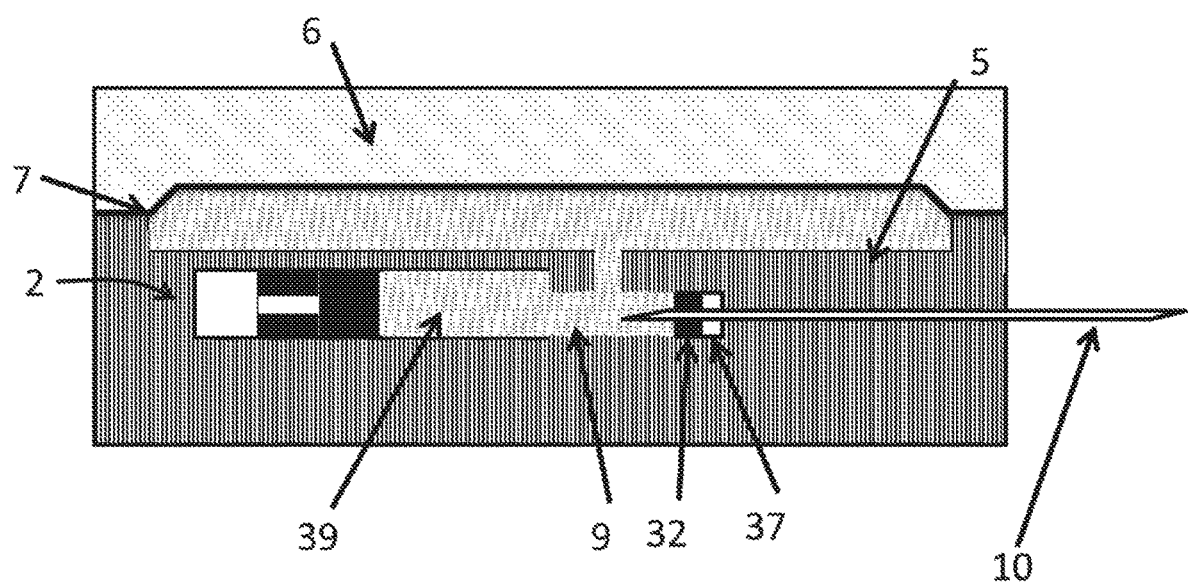

FIG. 21 shows an example of drug delivery system during injection, comprising a propellant reservoir (here butane at 20° C. for example), a drug reservoir tightly separated from the gas reservoir, a double beveled needle, an indicator device, and a valve device having a cylinder and a plunger which has been pierced by the needle after activation of the device. In the embodiment the indicator device is optional.

Figure 22A:
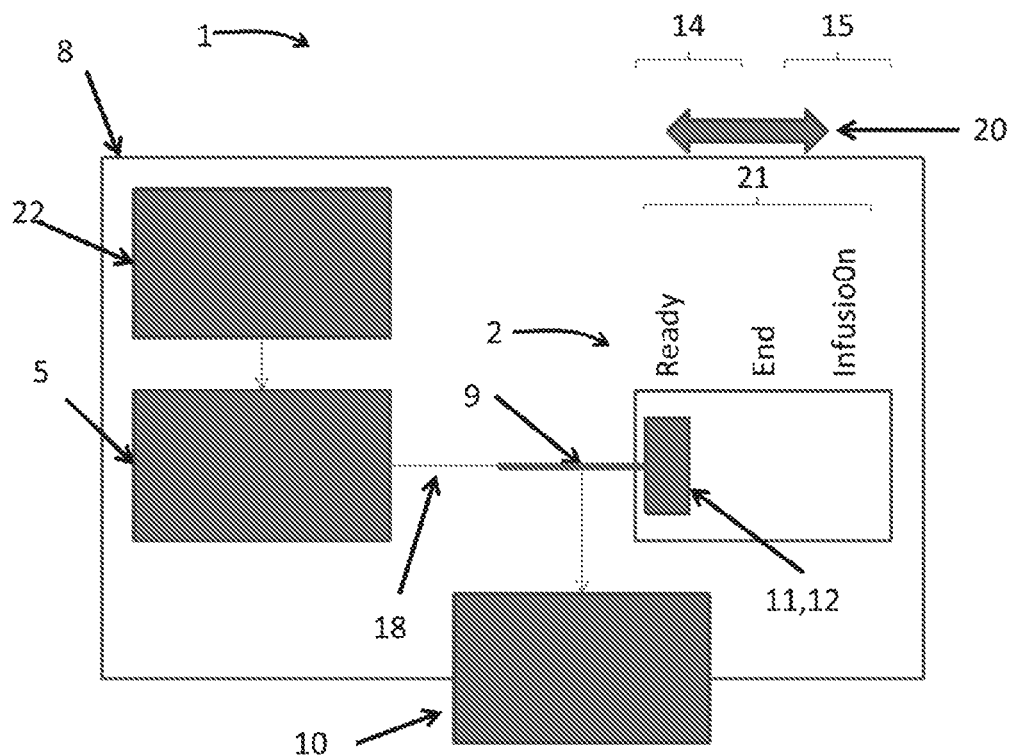
Figure 23A:
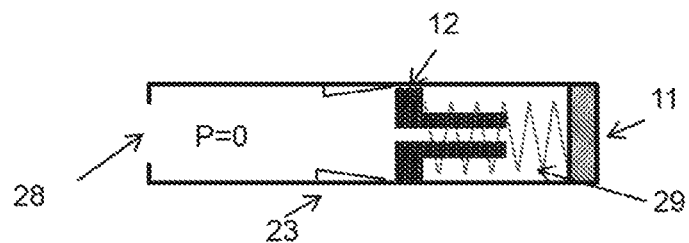
Figure 23B:
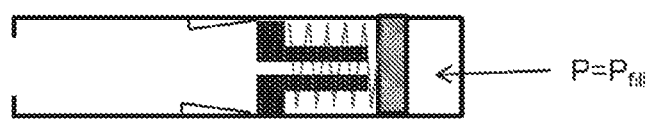
Figure 23C:
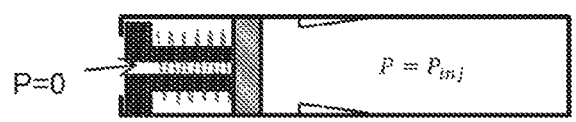
Figure 23D:

FIGS. 22a, b, and c show the general concept of the indicator device of the disclosure FIGS. 23a, b, c, d, e, and f show another potential embodiment of the disclosure.

FIG. 24 shows several views of a potential infusion status indicator.

Figure 25:
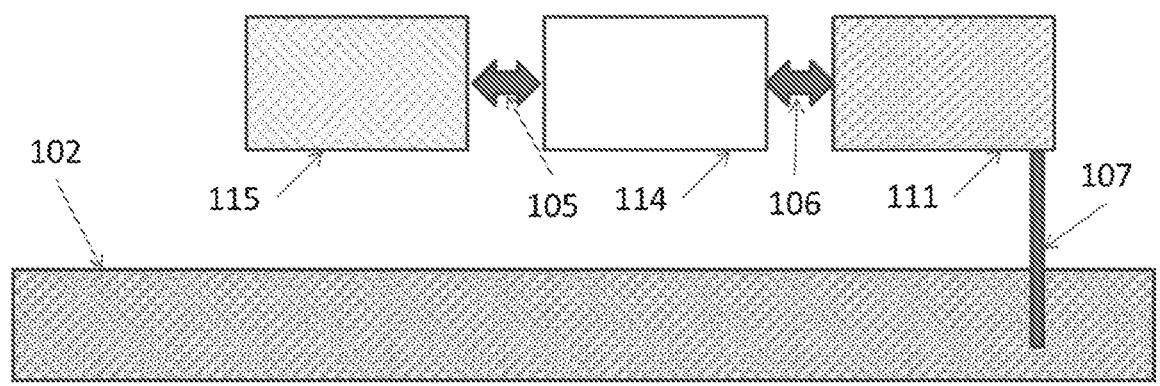

FIG. 25 shows a schematic view of a potential coupling according to an embodiment of a delivery system.

Figure 26:
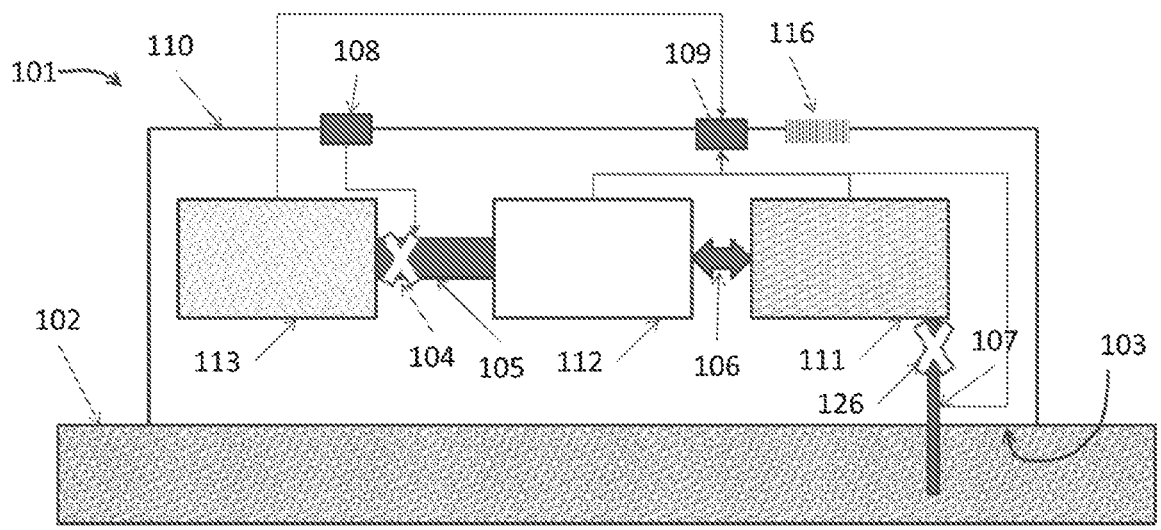

FIG. 26 shows a schematic view of the general structure according to an embodiment of a delivery system.

Figure 27A:
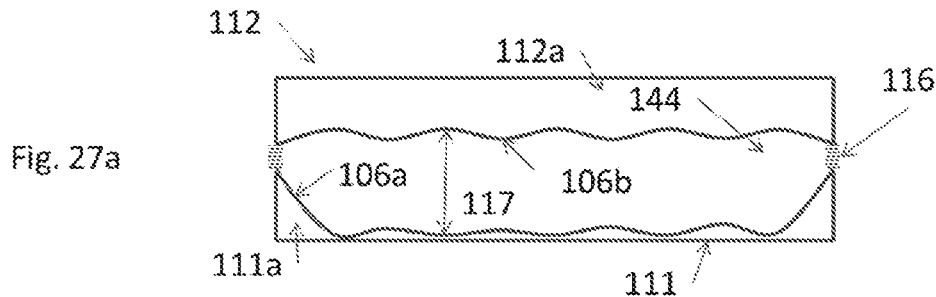
Figure 27B:
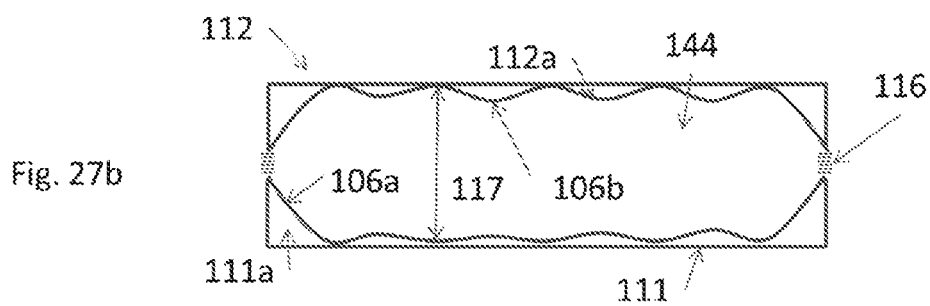

FIGS. 27a, b, c, d and e show schematic views of different status of a delivery system.

Figure 28A:
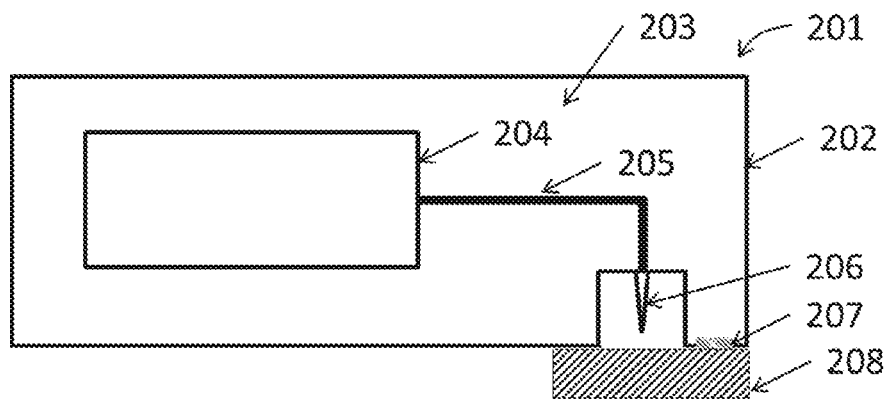
Figure 28B:
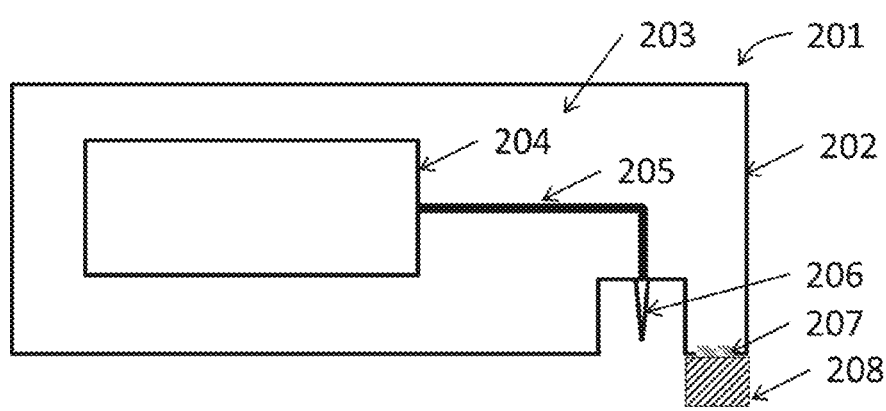

FIGS. 28a, b and c show potential embodiments of a delivery system.

Figure 29A:
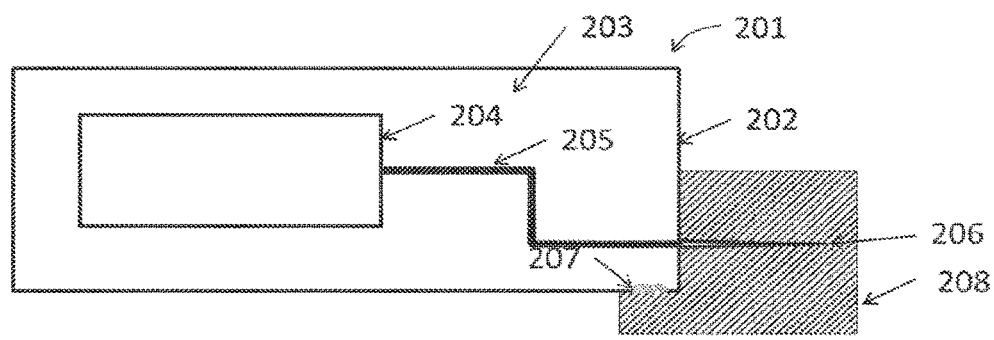
Figure 29B:
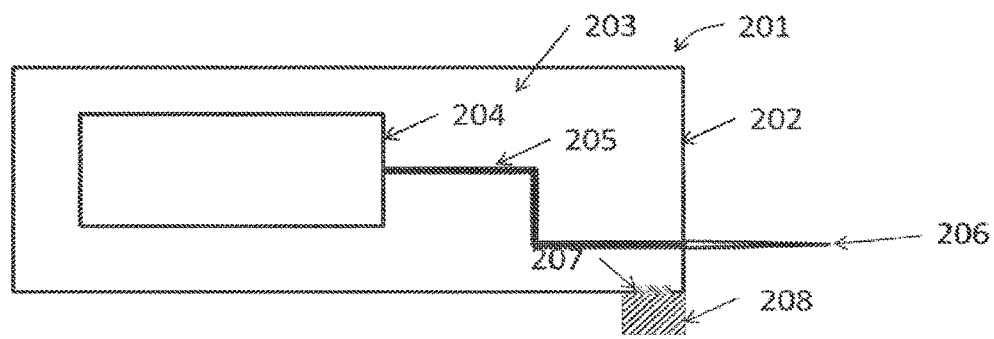

FIGS. 29a and b show potential embodiments of a delivery system.

Figure 30A:
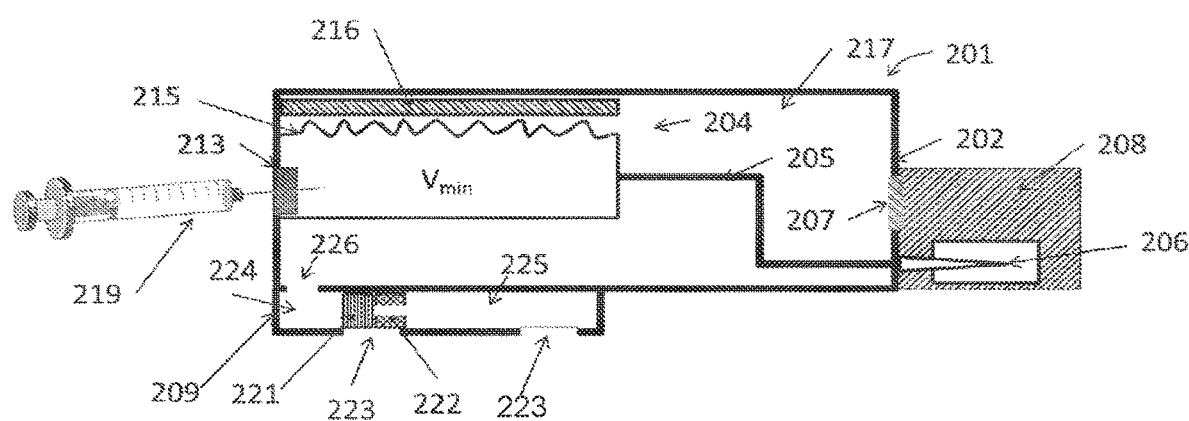

FIGS. 30a, b, and c show a delivery system comprising filling indicator device having a first and a second movable elements.

FIGS. 31a, b, and c show several views of a potential filling indicator device.

FIGS. 32a, b, c, d, and e show several views of a first side of potential indicator device.

FIGS. 32a', b', c', d', and e' show several views of a second side of potential indicator device.

Figure 33A:
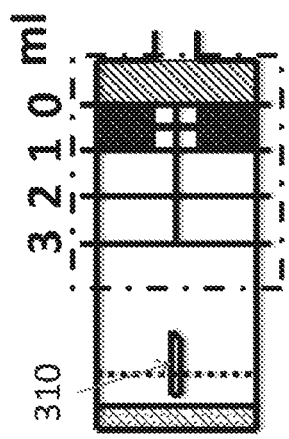
Figure 33A:
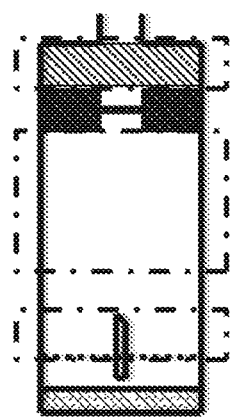
Figure 33B:
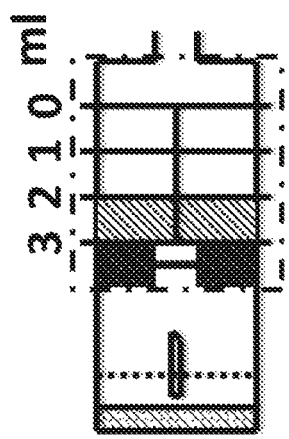
Figure 33B:
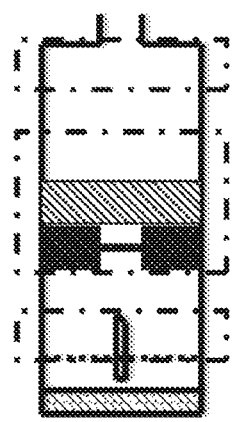
Figure 33C:
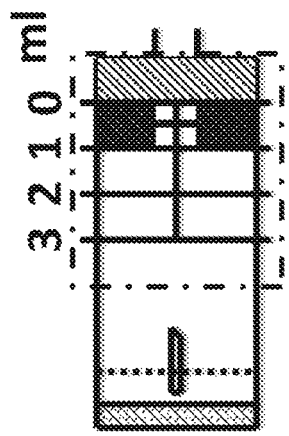
Figure 33C:
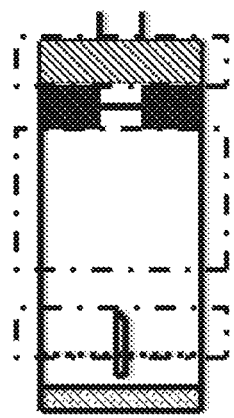
Figure 33D:
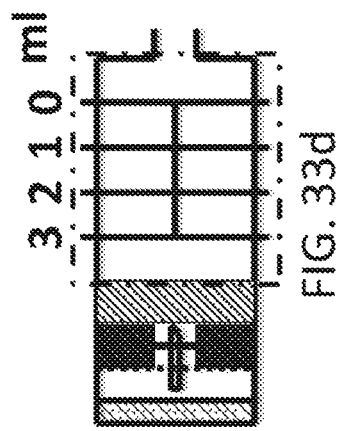
Figure 33E:
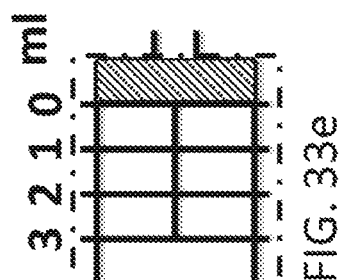
Figure 33D:
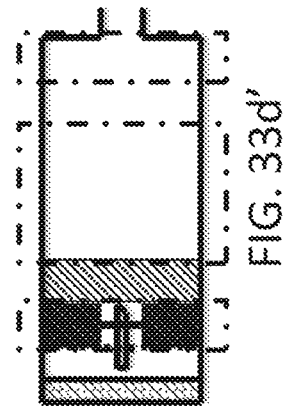
Figure 33E:
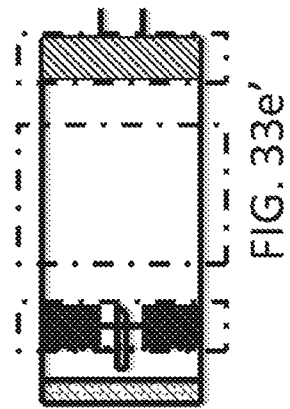

FIGS. 33a, b, c, d, and e show several views of a first side of potential indicator device.

FIGS. 33a', b', c', d'and e' show several views of a second side of potential indicator device.

Figure 34A:
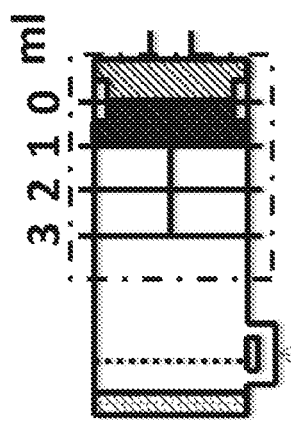
Figure 34B:
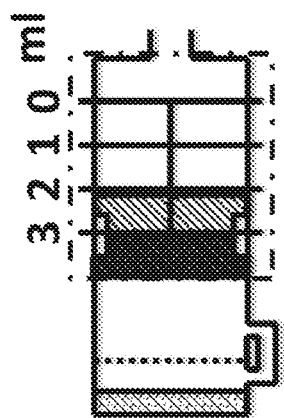
Figure 34C:
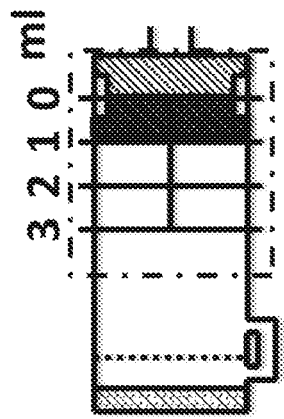
Figure 34A:
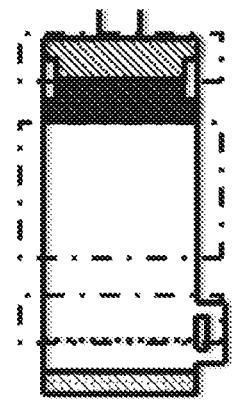
Figure 34B:
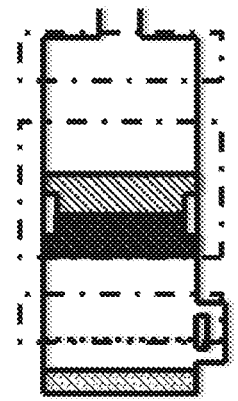
Figure 34C:
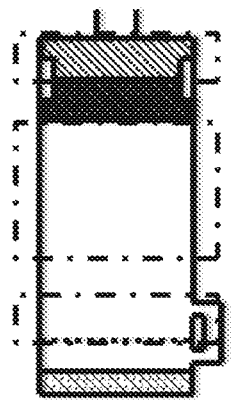

FIGS. 34a, b, c, d, and e show several views of a first side of potential indicator device.

FIGS. 34a', b', c', d', and e' show several views of a second side of potential indicator device.

Figure 35A:
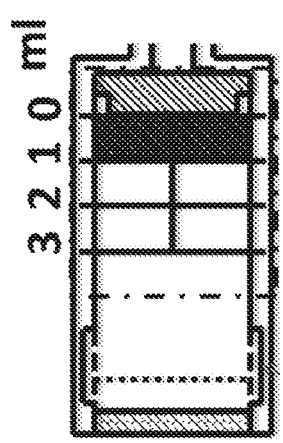
Figure 35A:
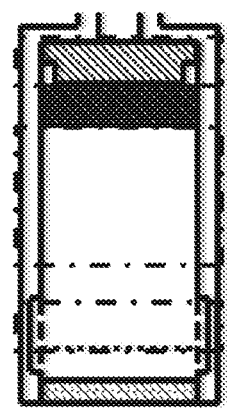
Figure 35B:
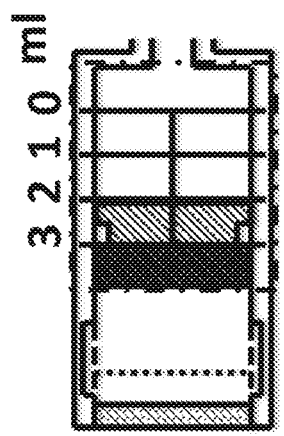
Figure 35B:
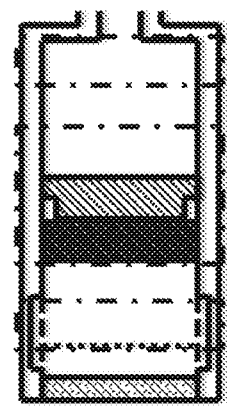
Figure 35C:
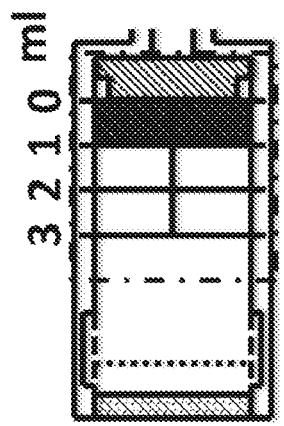
Figure 35C:
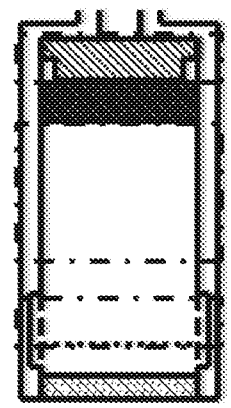
Figure 35D:
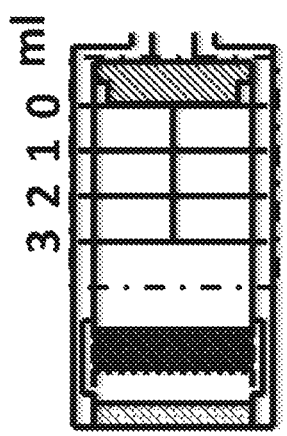
Figure 35D:
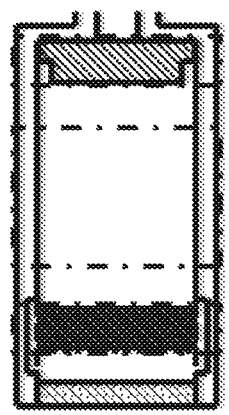
Figure 35E:
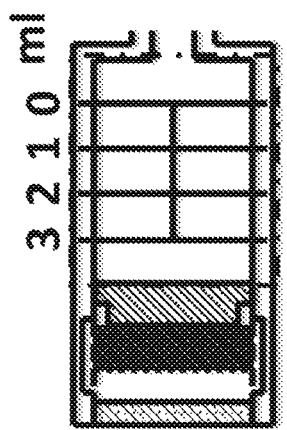
Figure 35E:
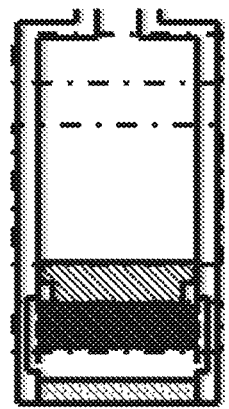

FIGS. 35a, b, c, d, and e show several views of a first side of potential indicator device.

FIGS. 35a', b', c', d', and e' show several views of a second side of potential indicator device.

FIGS. 36a, b, c, d, e and f show several views of a two other potential indicator devices.

Figure 37C:
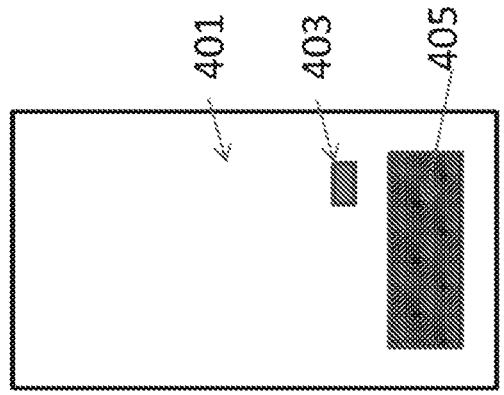
Figure 37B:
Figure 37A:
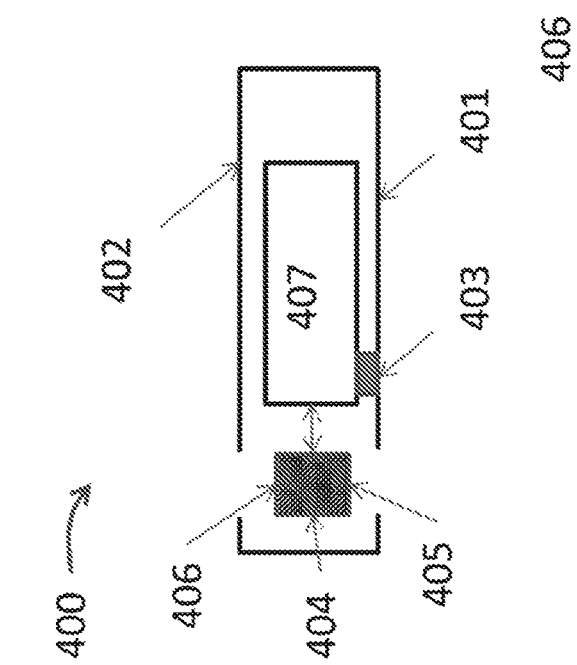

FIGS. 37a, b, and c, show several views of a potential delivery system.

Figure 38:
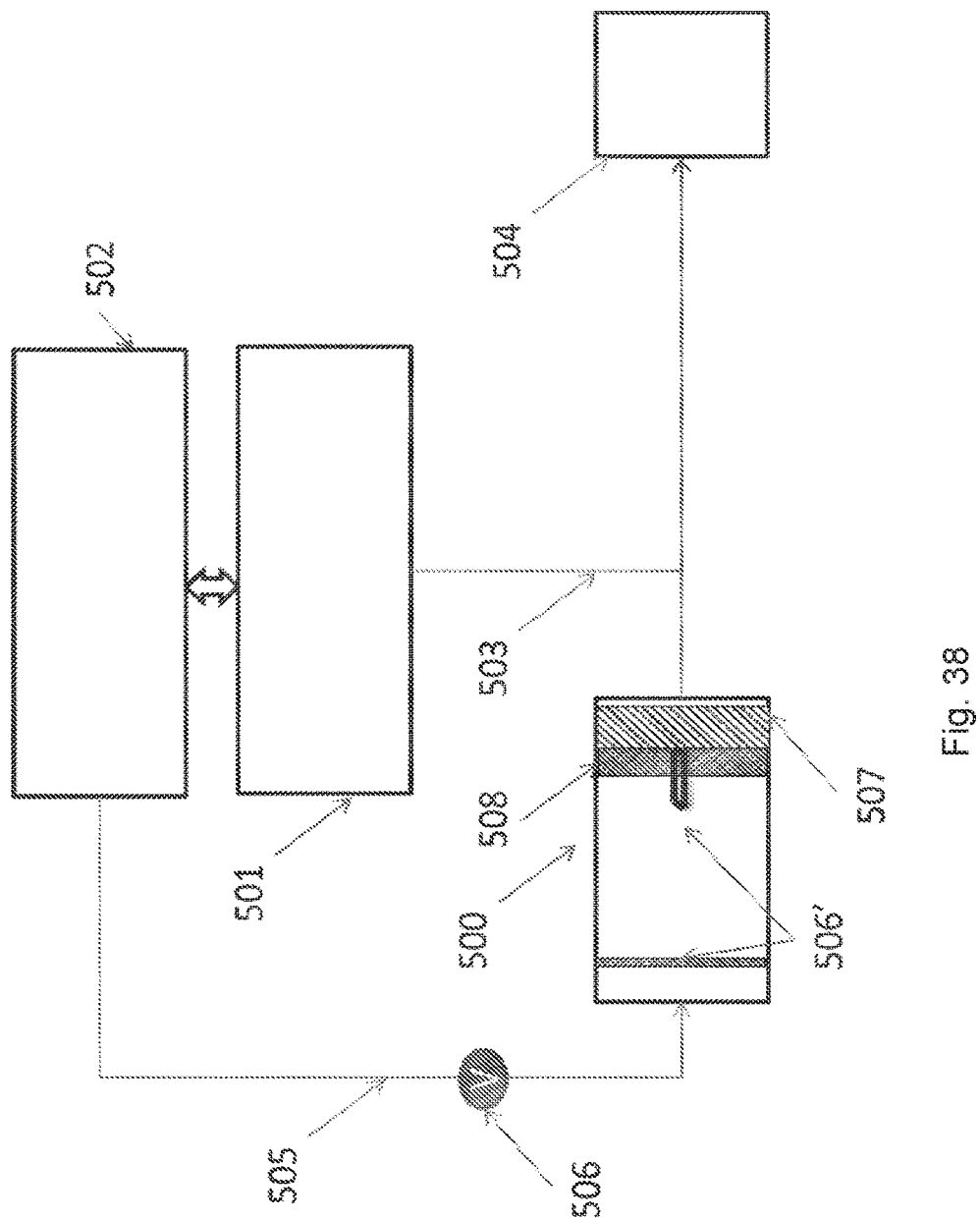

FIG. 38 shows a schematic view of a potential coupling according to an embodiment of a delivery system.

Figure 39:
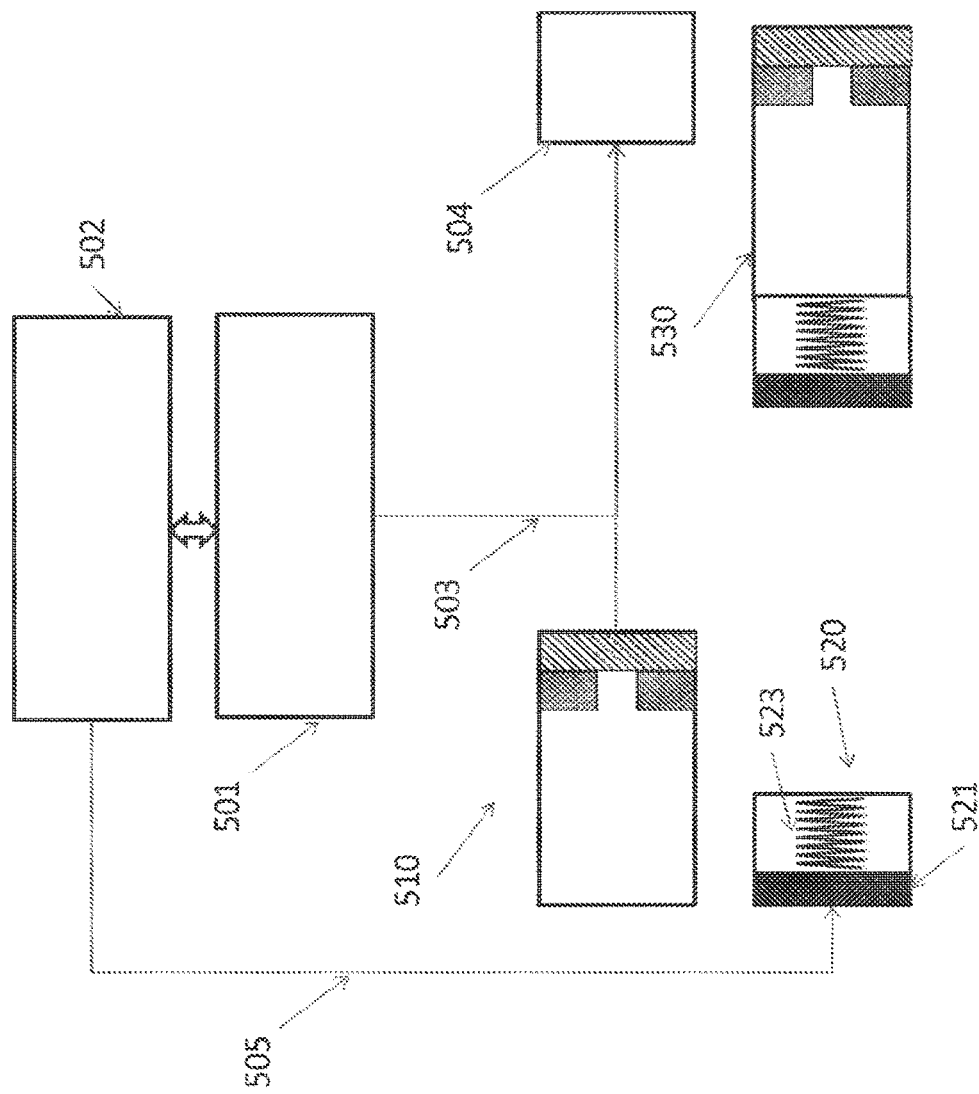

FIG. 39 shows a schematic view of a potential coupling according to an embodiment of a delivery system.

LIST OF ELEMENTS

1 Delivery device
2 Indicator device
3 Valve device
4 Pressure device
5 Drug reservoir
6 Propellant reservoir
7 Flexible or movable membrane
8 Housing
9 Communication port or fluid port
10 Outlet device
11 First plunger
12 Second plunger 13 Cavity
14 First end of the cavity
15 Second end of the cavity
16 Through hole
17 Venting device
18 Fluid pathway
19 Body
20 Linear movement displacement of the plunger(s)
21 Visual inscription
22 Pumping device
23 Stop member/mechanical stop
24 Window(s)
25 Spring/biasing element
26 Plunger stopper
27 Plug
28 Vent
29 Spring/biasing element
30 Elastomeric membrane
31 Compressible visual element
32 Movable septum or plunger
33 T-shape channel
34 First fluid port
35 Second fluid port
36 Third fluid port
37 Valve cavity
101 Delivery system
102 Patient
103 Skin-adherable unit
104 Valve device
105 Fluid pathway
106 Reservoirs' interface
106a First flexible membrane/movable wall
106b Second flexible membrane/movable wall
106c Third flexible membrane/movable wall
107 Injection device
108 Trigger device
109 Indicator
110 Housing
111 First reservoir
111a Storage compartment of the first container
112 Second reservoir
112a Storage compartment of the second container
113 Third reservoir
114 Pressurization device/means
115 Acting device/means
116 Vent device
117 Gap
121 Syringe
122 Inlet port
126 Valve device
201 Delivery system
202 housing
203 Cavity or internal compartment of the housing
204 Reservoir module
204a Internal compartment of the reservoir
205 Fluid pathway
206 Needle
207 Vent device
208 Removably occluding device
209 Indicator device or filling sensing or pressure transducer or pressure sensor
210 Indicator
212 Power supply
213 Inlet
214 Septum (piercable)
215 Movable wall
216 Pumping device
217 First cavity
219 Filling device
221 First plunger
222 Second plunger
223 Window
224 First volume
225 Second volume
226 Opening
300 Indicator device
301 First side
302 Second side
303 first movable element (such as a plunger)
304 Second movable element (such as a plunger)
305 Visual element
306 Indicator window
307 Fluid port
308 First end
309 Second end
310 Needle
311 Fluid pathway
312 Biasing means
400 Delivery system
401 First face
402 Second face
403 Inlet port
404 Indicator device
405 First side
406 Second side
407 Reservoir module
500 Indicator device
501 First reservoir
502 Second reservoir
503 Fluid pathway
507 Movable element
508 Movable element
510 First indicator device
520 Second indicator device
530 Indicator device

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense. The features described therein may be comprised in the different embodiments.

All scientific and technical terms used herein have meanings commonly used in the art unless otherwise specified. The definitions provided herein are to facilitate the understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and orientations.

As used herein, "have", "having", "include", "including", "comprise", "comprising" or the like are used in their open ended sense, and generally mean "including, but not limited to".

As used herein, the term "substantially" is a broad term and is used in its ordinary sense, including, without limitation, being largely but not necessarily wholly that which is specified.

As used herein, "at least one of A, B, and C", "at least one of A, B or C", "selected from the group consisting of A, B, C, and combinations thereof" or the like are used in their open ended sense including "only A, or only B, or only C, or any combination of A, B and C" unless the content clearly dictates otherwise.

As used herein, "plunger" or the like are used in it open ended sense, and generally mean a movable piece arranged into a cavity and configured to (optionally tightly) separates said cavity in two distinct parts.

As used herein, "cylinder" or the like are used in it open ended sense, and generally mean a solid formed by a line that moves parallel to itself by leaning on a flat curve.

As used in this specification and the appended claims, the term "or" is generally employed in its sense including "and/or" unless the content clearly dictates otherwise.

The present application claims the benefit of the priority of EP18157250.4 filed on 16 Feb. 2018 in the name of Debiotech SA, the entire disclosure of which is incorporated herein by reference. Furthermore, the present application claims the benefit of the priorities of EP18182850.0 filed on 11 Jul. 2018, of EP18215745.3 filed on 21 Dec. 2018, of EP19151323.3 filed on 11 Jan. 2019, of EP19151324.1 filed on 11 Jan. 2019, of EP19151325.8 filed on 11 Jan. 2019, and of EP19155800.6 filed on 6 Feb. 2019 in the name of Debiotech SA, the entire disclosure of which are incorporated herein by reference.

Example of Operating Principle

Figure 22B:
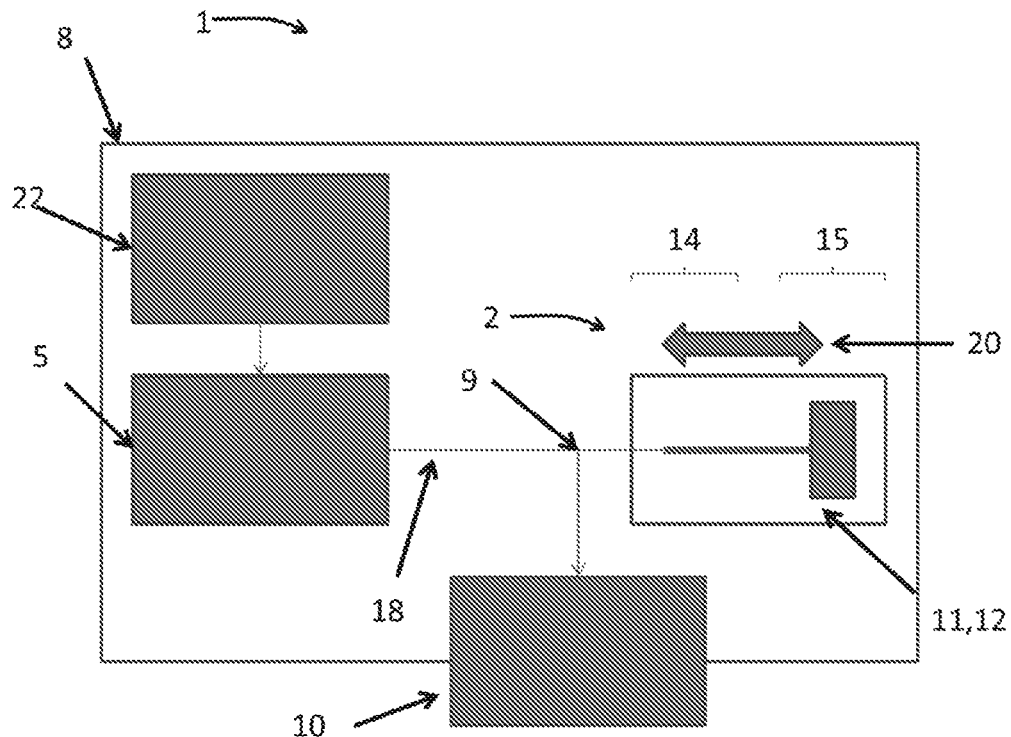
Figure 22C:
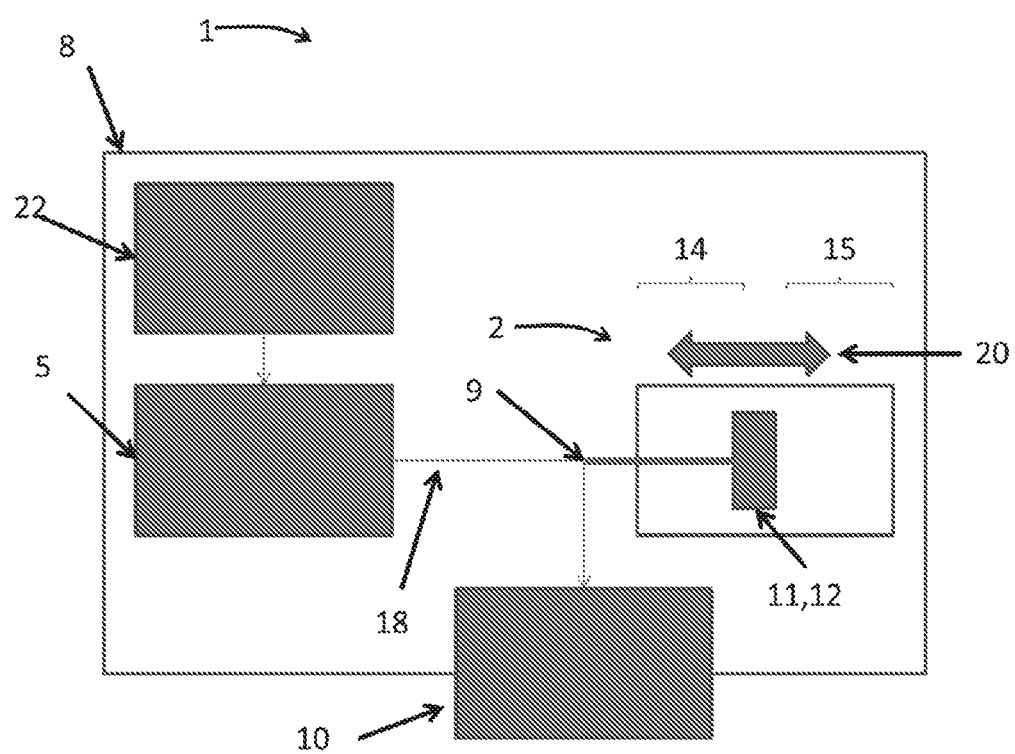

The FIGS. 22a, 22b and 22c show an example of a general concept of an indicator device as described in this document. The shape and the size are not representative. In these figures only one movable element is drawn but the basic concept stays identic for two movable elements, thus both references are used for the movable element (11, 12). In these figures the indicator device indicates information relates to the state of the infusion but the basic concept stays identic for other embodiments described in this document.

The delivery system (1) comprises a reservoir (5) adapted to store a medical fluid (for example a drug or other solution which may be infused to a patient, preferentially an incompressible fluid such as a liquid), a pumping device (22) adapted to move the medical fluid stored in the reservoir, an outlet device (10) (for example an outlet port or an transcutaneous device) adapted to be in fluid communication with a patient, and a fluid pathway (18) providing a fluid communication between the reservoir (5) and the outlet device (10).

In order to simplify the description, the reservoir (5) is also called drug reservoir but this wording does not limit the type of fluid which may be stored in the reservoir. For example, the drug reservoir may store a solution, for example a liquid solution, preferentially a medical fluid such as pharmaceuticals, nutritional formulas, biologically derived or active agents, hormonal and gene based material, and other substances.

The drug reservoir (5) may comprise a movable wall (for example a plunger, a flexible membrane or other). The drug reservoir may further comprise a rigid part.

At least one of the movable wall and the rigid part define an internal compartment intended to receive the medical fluid to be infused to the patient. The drug reservoir may further comprise one or more outlet. The outlet of the reservoir is in fluid communication with at least one of the patient, outlet device (10), and the indicator device (2). Preferentially, the fluid pressure in the drug reservoir is substantially transmitted into at least a part of the fluid pathway and/or to the indicator device.

Preferentially the pumping device comprises a pressure device adapted to apply a pressure to the drug reservoir (for example on the movable wall of the drug reservoir (5)) in order to move the medical fluid outside from the internal compartment of the drug reservoir (for example via its outlet). The pressure device may comprise a spring, a propellant chamber containing for example a liquefied gas, an expandable battery, a gas generating cell, a nitinol wire, a belleville washer, a belleville spring, Expancel beads, shape memory alloy, shape memory polymer, plunger, . . . .

In some embodiments, the pumping device is configured to infuse the entire content of the reservoir as a single bolus.

The outlet device (10) may comprise a connection port, an outlet port, a needle, a cannula, a tube, a connector or a transcutaneous device, . . . .

Preferentially, the indicator device (2) comprises a body in which is arranged a cavity (13) (also called cylinder even if the shape may be not essential). The cavity (13) may comprise a first end (14) and a second end (15); both may define a main axis. At least one movable element (11, 12) is arranged into the cavity and is configured to move relative to the cavity, for example along the main axis or in a direction parallel to the main axis. At least one movable element is configured to move depending on the pressure of the solution (for example the pressure present into the drug reservoir). At least one movable element may comprise a plunger.

In some embodiments, the indicator device indicates the infusion status thanks to a single plunger (for example via a back-and-forth motion). In another embodiment, the indicator device indicates the delivery system status by using two or more distinct plungers (for example at least one of a first plunger and a second plunger).

Preferentially, the indicator device is in pressure communication with at least one of the drug reservoir and the outlet device. For example, the pressure present into the internal compartment of the drug reservoir may be transmitted to the indicator device, in such a way to move at least one movable element through the cavity.

The indicator device may be in fluid communication with the internal compartment of the drug reservoir (and/or with the outlet device) in order to transmit the fluid pressure to the indicator device. More particularly, the outlet of the drug reservoir (5) may be in fluid communication and/or in pressure communication with the indicator device (2).

In some embodiments, the outlet of the reservoir is in fluid communication with the patient and the indicator device. In this case, during the drug delivery, a part of the medical fluid (intended to be infused to the patient) fills at least partially the cavity (for example the first variable volume as described in this document) and at the end of the delivery, a biasing means induces a back motion of at least one of the movable element which drains the cavity and injects to the patient the remaining medical fluid (temporarily stored into the cavity of the indicator device).

The fluid pathway may comprise a T-shaped channel adapted to receive the solution at a pressure substantially equal to the fluid pressure in the drug reservoir. The T-shaped channel may comprise a first fluid port in fluid communication with the outlet of the reservoir, a second fluid port in pressure communication and/or in fluid communication with the indicator device, and a third fluid port in fluid communication with an outlet device (and/or in fluid communication or in pressure communication with the valve device). The T-shaped channel is configured to provide a fluid communication from at least one of the first fluid port, the second fluid port and the third fluid port to one of the other said fluid ports. The T-shaped channel is described herein to explain the principle; other types of channel may provide the same technical feature.

A valve device may be configured to occlude at least one of the first fluid port, the second fluid port and the third fluid port. The first fluid port may be configured to allow the solution to flow from the internal compartment of the reservoir (from the outlet of the reservoir) to the T-shaped channel, the second fluid port may be configured to be operatively coupled with the indicator device and the third fluid port may be configured to allow the solution to flow from the T-shaped channel to the outlet device.

The T-shaped channel may be in fluid communication with an inlet port of the delivery system. The T-shaped channel may further comprise an additional port in fluid communication with the inlet port of the delivery system. Said inlet port of the delivery system may be configured to be in fluid communication of the internal compartment of the drug reservoir.

According to the FIGS. 14 and 22, a part of the plunger may extend through a part of the T-shaped channel when the plunger is in a determined position (for example first position and/or third position).

The drug reservoir may comprise an inlet adapted to fill the drug reservoir with a solution to be delivered (for example if the drug reservoir is initially or sold empty). The inlet may be in fluid communication with the inlet port of the delivery system. The inlet may be distinct from the outlet of the reservoir. In another embodiment, the inlet may also be the outlet of the reservoir. In this case, the outlet of the reservoir is in fluid communication with the inlet. Furthermore, the inlet of the drug reservoir may be in fluid or pressure communication with the indicator device. In this case, the indicator device may be also used to provide information related to the fill of the drug reservoir.

The delivery system may comprise a housing in which the drug reservoir (5), the pumping device (22), the valve device (3), the fluid pathway (18) and/or the indicator device (2) may be at least partially arranged.

According to the FIG. 22a, the plunger device (11, 12) is in an initial positon which may indicate that the delivery system is ready to infuse or ready to use. This status may be an initial status of the delivery system.

If the plunger device comprises a valve device (3), when the plunger is in the initial position, the valve device may occlude the fluid pathway between the reservoir and the outlet device. This valve device may prevent the solution from reaching the outlet device before the activation of the delivery system, for example when the user fills the drug reservoir. The valve device may be a rod inserted into a part of the fluid pathway and mechanically coupled to the movable element (for example a first plunger) or a part of the plunger as described below.

Focus now to the FIG. 22b, after an activation of the delivery system, the drug reservoir (5) is pressurized by the pressure device, the medical fluid flows through the fluid pathway and moves the movable elements (11, 12) relative to the cavity (for example linearly (22), according to an axe defined by two ends of the cavity). The volume defined between the first movable element and the first end of the cavity increase and may receive a volume fraction of the medical fluid. The movable element moves toward a determined position and the indicator device indicates that the infusion is in progress. This position may be maintained until the drug reservoir is empty.

If the movable element is in fluid communication with the medical fluid then the cavity comprises a fluid port, and a volume fraction of the medical fluid fills a part of the cavity (between the end comprising the fluid port and the plunger device).

If the indication device (2) comprises only one movable element then this movable element is moved. If the indicator device comprises two distinct movable element then both movable element are moved, for example, the fluid pressure moves the first movable element and the first movable element may move the second movable element (for example pushed by the first movable element or due to the compressed gas store between the first and the second movable element). During this phase, the volume between the second movable element and the second end of the cavity decreases. If the second end does not comprise any vent then the gas in this volume is compressed.

If the indicator device comprises a valve device (3), when the pressure device is activated the fluid pressure in the drug reservoir increases and reaches a determined threshold needed to open the valve device.

Focus now on the FIG. 22c, when the drug reservoir is emptied, the fluid pressure of the medical fluid decreases until reaching the atmospheric pressure (or interstitial pressure if the outlet device comprises a transcutaneous device). The indicator device may be configured to allow at least one of the first movable element and the second movable element to move toward the first end in order to indicate that the infusion is over. The volume between the first movable element and the first end decreases. If this volume has received a volume fraction of the medical fluid, the movable element motion expels the solution through the pathway to the outlet device.

The cavity may exhibit a cylindrical or quadrilateral shape.

Figure 1:
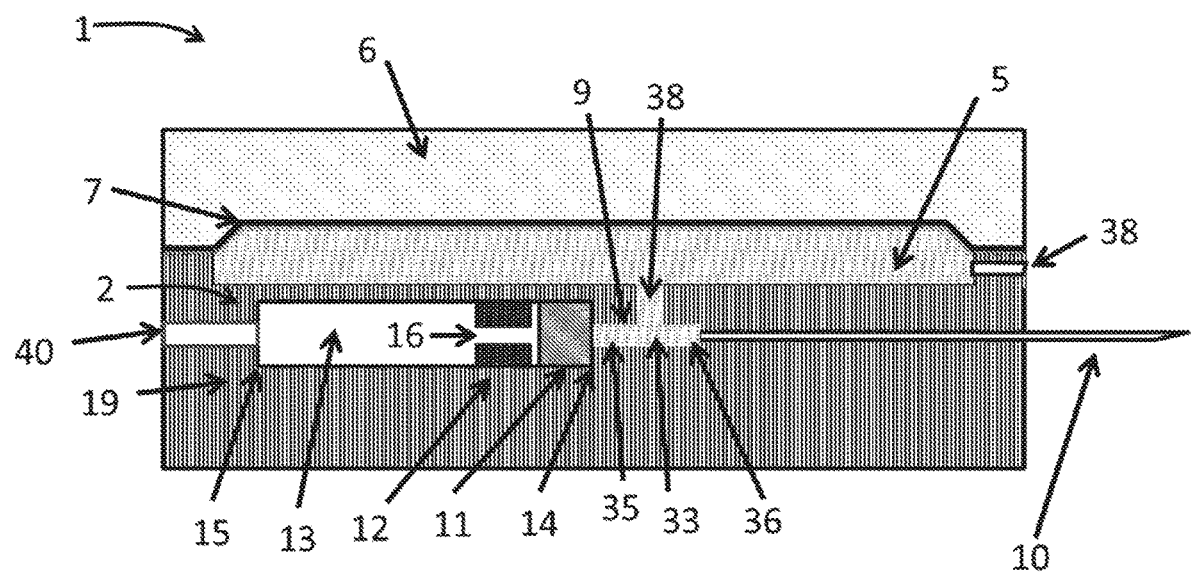
FIG. 1 shows an embodiment of the drug delivery system before injection, comprising a propellant reservoir (here liquefied gas), a drug reservoir tightly separated from the gas reservoir and an indicator device having two plungers.
Figure 2:
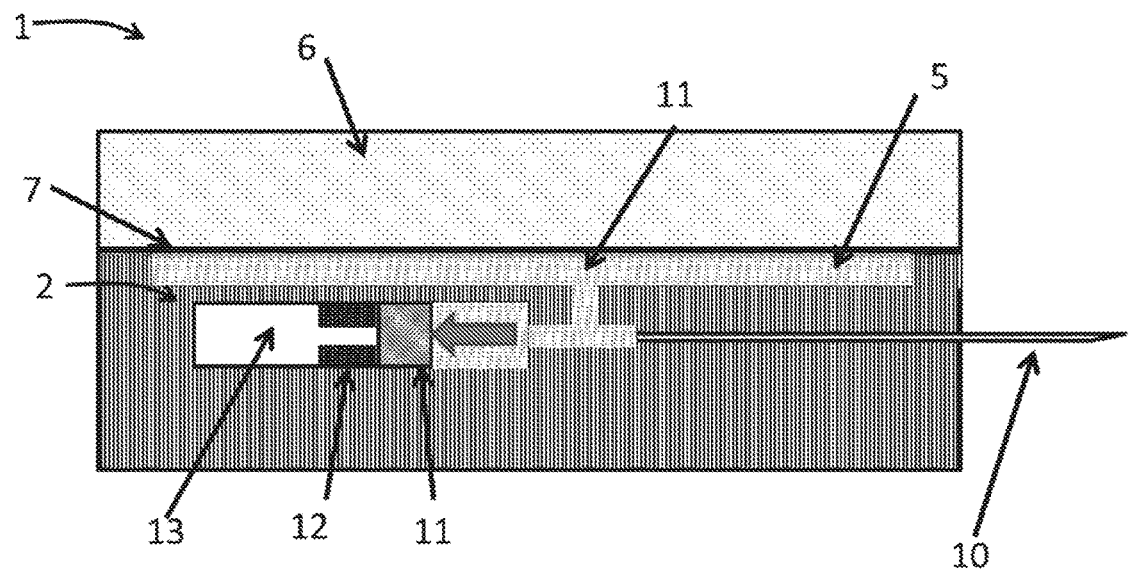
FIG. 2 shows the same device (of the FIG. 1) after activation, the membrane between the propellant and drug reservoir transmitting the gas pressure to the drug. The two plungers are translated to the left part of the cylinder until the air pressure in the left part of the cylinder becomes substantially equal to the drug reservoir pressure.
Figure 3:
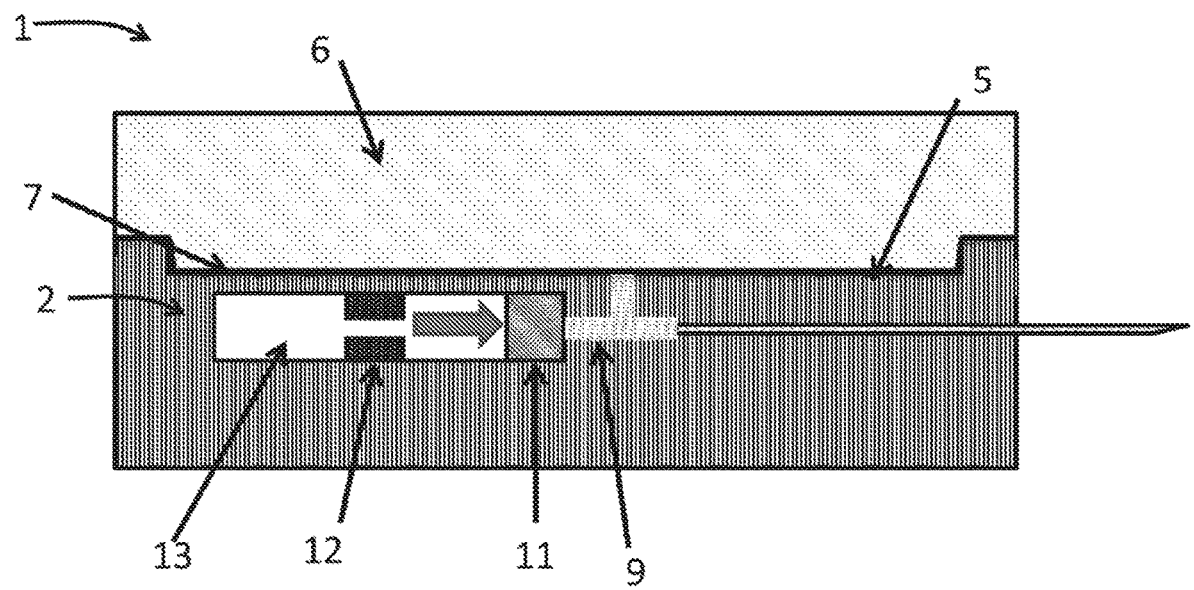
FIG. 3 shows the same device (of the FIG. 1) at the end of the injection, wherein the pressure in the communication port drops to zero, inducing a movement of the solid plunger toward its initial position.

The FIG. 1 shows an optional vent (40) which may be required in some embodiments.

Example of Delivery System

An example of a delivery system adapted to comprise an indicator device is disclosed thereafter and by the European application EP18182850.0 filed on 11 Jul. 2018 and EP19151324.1 filed on 11 January in the name of Debiotech SA, the entire disclosure of which is incorporated herein by reference.

As shown by the FIG. 25, the delivery system (101) may comprise a first reservoir (111) adapted to store a medical fluid (such as a drug or a pharmaceutical fluid or other fluids). The medical fluid may be a liquid or a gas, for example an incompressible fluid, and is intended to be delivered to a patient (102) for example via a transcutaneous device (107). The transcutaneous device (107) may be in fluid communication with the first reservoir (111) and may comprise for example a needle, a cannula, one or more micro needle or other means adapted or configured to bring the medical fluid into or on the patient body.

The delivery system (101) may further comprise a pressurization means (114) which may be operatively coupled (106) to the first reservoir (111). For example, the pressurization means (114) may be adapted or configured to pressurize the first reservoir so as to cause the flow of the medical fluid from the first reservoir (111) to the patient (102). For example if the first reservoir (111) comprises a movable wall (for example a flexible membrane), the pressurization means (114) may be configured to act on the movable wall in order to pressurize the first reservoir.

In some embodiments, the pressurization means may comprise a propellant chamber containing for example a liquefied gas having a vapor pressure at 20° C. comprised in the range [+0.1 bar; +10 bar]. The device may include a valve that is opened during the system activation, allowing the pressurization of the first reservoir (111) for example by transmitting the pressure on a movable wall of the first reservoir (111).

The delivery system (101) may further comprise an action means (115) which may be operatively coupled to the pressurization means (114). For example, the action means (115) may be adapted or configured to allow the pressurization of the first reservoir.

In some embodiments, the pressurization means may comprise a second reservoir and the action means may comprise a third reservoir in fluid communication or pressure communication with the pressurization means. The action means may further comprise a valve device and a fluid pathway allowing a fluid communication between the second reservoir (of the pressurization means) and the third reservoir (of the action means) for example when the valve device is in open position.

The third reservoir of the action means may be configured or adapted to store a compressed fluid such as a propellant. The propellant may be a liquefied gas that exhibits a large value of vapour pressure at ambient temperature. The pressure range is therefore determined by the evolution of this vapour pressure within a predefined range of functioning temperature, typically from 5° C. to 40° C. Considering isobutene as propellant, this pressure (absolute) is for instance 1.86 bars at 5° C., 3 bars at 20° C. and 5.25 bars at 40° C.

According to another embodiment, the pressurization means (114) may comprise a spring, an elastic device, an actuator which acts on the first reservoir (for example on a movable wall, a flexible wall, a plunger, . . . ). And the actions means (115) may comprise an element adapted to release or generate a gas, such as a battery or other chemical elements, or to act on the pressurization means (114) . . . .

The delivery system may be intended for single use. Thus, after a single use/delivery, the delivery system may be discarded, for example entirely discarded.

The delivery system may be configured to deliver the entire volume of the solution stored in the first storage compartment in a single bolus. Thus, once the trigger device is activated, the delivery system will infuse the solution to the patient until the first storage compartment is substantially empty.

The delivery system may be adapted to inform the patient of the end of the delivery, via the indicator device as disclosed in this document.

Preferentially, the delivery system does not comprise any electronic element configured to convey the solution and/or to pressurise the first reservoir and/or to control the pressurization means (114) and/or the action means (115).

Nevertheless, in some embodiments, the delivery system may comprise an electronic device configured to control and/or monitor the delivery. For example, an indicator device may comprise some electronic elements such as a pressure sensor, a processor and/or a light indicator (LED, . . . ). But, preferentially, the delivery system and the indicator device are configured to operate without any electronic element and/or battery.

The delivery system (101) disclosed by the FIG. 26 comprises at least one of:
A first reservoir (111)
A second reservoir (112), and
A third reservoir (113).

In some embodiments, the first reservoir (111) comprises a first storage compartment, a first movable wall (for example a flexible wall/membrane) configured to change a capacity of the first reservoir (111) (for example the volume of the storage compartment) and an outlet port allowing the solution to get out of the storage compartment. The outlet port is configured to be in fluid communication with the transcutaneous device (107), for example when the delivery system delivers the solution to the patient.

The first reservoir may comprise an inlet port to fill the storage compartment with a solution intended to be delivery to the patient (for example a medical fluid). The inlet port and the outlet port may be the same port or the inlet port may be a different port from the outlet port.

In some embodiments, the second reservoir (112) comprises a second storage compartment, a second movable wall (for example a flexible wall/membrane) configured to change a capacity of the second reservoir (112) (for example the volume of the second storage compartment). More particularly, a change of the volume of the second storage compartment induces a movement of the second movable wall (for example a movement/deformation/stretching of the flexible membrane). The second reservoir may comprise an inlet port. The second reservoir (112) may comprise an outlet port configured to expel the propellant from the second reservoir for example at the end of the delivery.

Preferentially, the first reservoir (111) and the second reservoir (112) comprise a reservoirs' interface (106) configured in such a manner that the first reservoir and the second reservoir are in pressure communication when the first movable wall and the second movable wall are at least partially in contact.

In some embodiments, the third reservoir (113) comprises a third storage compartment (113a) configured to store a compressed fluid (in a compressed state) such as a propellant. The third reservoir may comprise rigid walls in such a manner the volume of the third storage compartment is constant. The third reservoir comprises an outlet port configured to be in fluid communication with the second storage compartment in a delivery state in such a manner that the compressed fluid flows from the third storage compartment to the second storage compartment.

The delivery system may further comprise an indicator device (109). The indicator device may be operatively coupled (for example in pressure communication or in fluid communication or other) to at least one of the first reservoir, the second reservoir, the third reservoir and the transcutaneous device. The indicator device (109) may be configured to provide an information to the user concerning the status of the delivery system or filling process or one of the listed elements, for example: Occlusion, ready, ready to be activated, ready for filling, ready to infuse, delivery in progress, error, full storage compartment, empty storage compartment, delivery finished, . . . .

The delivery system may comprise a skin-adherable unit (103) configured to secure the delivery system to the patient skin. The skin-adherable unit may comprise a first side having an adhesive surface facing toward the skin surface of the patient for adhesion and a removable cover for covering the skin-adherable unit. The skin-adherable unit may further comprise a frame and coupling device configured to (optionally removably) secure the delivery system.

The delivery system may further comprise at least one of a trigger device (108), a vent device (116), one or more valve device (104, 126), and a fluid path way (105), . . . .

As disclosed by the FIGS. 27 a, b, c, d and e, the reservoirs' interface (106) may comprise a cavity defined by at least a first surface (106a) of the first movable wall and a second surface (106b) of the second movable wall. Preferentially, the first surface (106a) is arranged opposite to the second surface (106b). The reservoirs interface (106) may be configured in such manner that the first surface (106a) may be:

spaced apart from the second surface (106b), when the delivery system is in a first state (for example an initial state of the delivery system), and/or in contact with the second surface (106b) when the delivery system is in a second state (for example a delivery state of the delivery system).

The cavity of the reservoirs' interface may have a variable volume depending on the delivery state and/or the filling state. This cavity is preferentially vented by a vent device (116) as described below.

The vent device (116) (for example an aperture) is intended to allow a fluid communication between at least an inside part of the delivery system and the outside environment of the delivery system. The vent device may be configured to keep the cavity of the reservoirs' interface (106) vented. In particular, the vent device may be configured to provide a pressure equilibration of the reservoirs' interface cavity when at least one of the first storage compartment volume and the second storage compartment volume varies. Nevertheless, the system may comprise an occluding device configured to occlude the vent device (116) at least during a filling process or a storing period.

The venting device may comprise a hydrophobic membrane, a filter or a coating configured to prevent the flow of water into the enclosure. The venting device may comprise a baffle configured to prevent the insertion of a straight and rigid tip.

An example of vent device which may be comprised in the delivery system is described by the United States Patent: U.S. Pat. No. 9,872,955, the entire disclosure of which is incorporated herein by reference.

The FIGS. 27 a, b, c, d and e show different potential states of the delivery system, in particular the first and the second reservoir.

Initial State:

In some embodiments, as disclosed by the FIGS. 27a and b, the first storage compartment may not initially store the medical fluid (for example before the delivery, when the delivery system is in the packaging), the volume of the first storage compartment may be initially minimal. In this case, the first storage compartment is initially substantially empty. The movable wall may be in contact (or very close to or in the closest manner) with the opposite internal wall of the first reservoir (for example on a substantial length of the first storage compartment), for example against the internal wall of the rigid part of the first reservoir (111).

In another embodiment (for example as the state of the system shown by the FIG. 27d), the first storage compartment may initially store the medical fluid. In this case, the volume of the first storage compartment may be maximal.

In both cases, preferentially, the movable walls of the first and the second reservoirs are not in contact in order to not exert any non-intentional pressure to the first reservoir.

Furthermore, the reservoirs' interface may be vented by the vent device. Or a removably occluding device may occlude temporarily the vent device.

At the initial state of the delivery system, the gap (117) between the first surface (106a) of the first movable wall and a second surface (106b) of the second movable wall may be maximal and/or the volume of the reservoirs' interface cavity (144) may be maximal.

Preferentially, the volume of the second storage compartment is initially minimal. Nevertheless, the second storage compartment may be non-empty and initially store a fluid such as a gas (for example air trapped during the manufacturing process).

As the third reservoir (not shown by the FIG. 27) preferentially comprises only rigid walls, the volume of the third storage compartment is constant. And, the third storage compartment may or may not initially store the compressed fluid.

Filling Step:

If the first storage compartment does not initially store the medical fluid, the user has to fill the first storage compartment before use and the first reservoir may comprise an inlet port configured to fill the first storage compartment with the medical fluid.

Figure 27C:
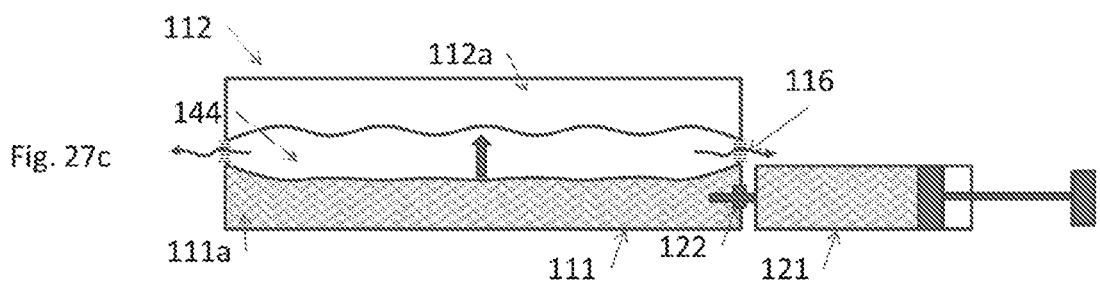
Figure 27D:
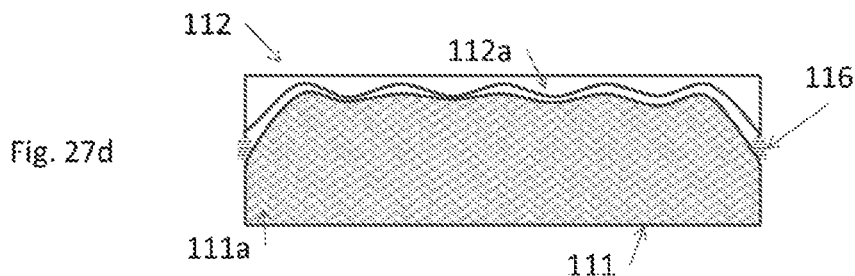
Figure 27E:
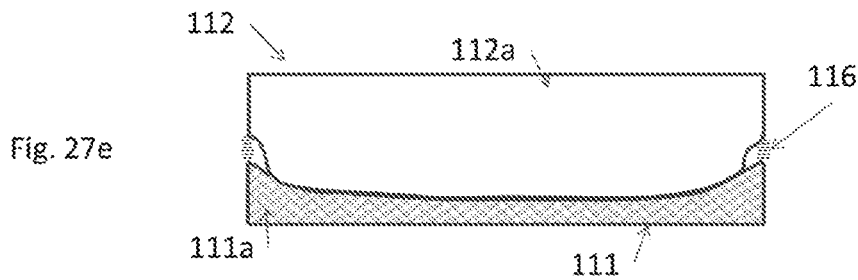

The FIG. 27c shows the filling of the first reservoir via a syringe (121), the volume of the first storage compartment increases and the volume of the reservoirs' interface cavity (144) decreases. The first surface (106a) of the first movable wall moves toward the second reservoir, for example toward the second surface (106d) of the second movable wall. The fluid (for example the gas trapped into the reservoirs' interface cavity) may be discharged/expelled to outside of the delivery system through the vent device (116). In the case where the vent device is (are) clogged or occluded by a removably occluding device, the pressure in the first storage compartment (111a) and/or the pressure in the reservoirs' interface cavity (144) will increase as the first reservoir is filled. As described by this document, the indicator device may detect this pressure increase and may provide a filling indication to the user.

If the third storage compartment does not initially store the compressed fluid, the user has to fill the third storage compartment before use and the third reservoir may comprise an inlet port configured to fill the third storage compartment with the compressed fluid.

Full Drug State:

At the end of the filling step, the gap between the first surface (106a) of the first movable wall and a second surface (106b) of the second movable wall is substantially reduced. The first surface (106a) of the first movable wall and a second surface (106b) of the second movable wall may or may not be in contact. The pressure exerted on the first movable wall, if any, must be limited and not induce a flow of the solution to the patient.

At this state the indicator device may indicate that the delivery system is ready to infuse or the drug reservoir is full.

Activated/Delivery State:

After the trigger device has been activated (for example as soon as or after a predetermined time period), the trigger device initiates a change of the delivery system state. The valve device (104 as disclosed by the FIG. 26) switches from a first state/position (closed position) to a second state/position (open position). A second state/position of the valve device induces a flow of the compressed fluid from the third storage compartment to the second storage compartment. The second movable wall moves toward the first reservoir due to the fluid pressure of the compressed fluid. The fluid pressure of the compressed fluid into the second reservoir induces a displacement (a bending) of the second movable wall which exerts a pressure on the first movable wall.

At least during the delivery, the second movable wall is configured to come into contact with the first movable wall on at least 50, preferentially at least 80%, more preferentially at least 90% for example (substantially) on 100% of the first movable wall surface.

The fluid pressure of the second reservoir is transmitted (at least partially or substantially) to the first reservoir, in particular to the solution stored in the first storage compartment. Furthermore, the pressure causes a flow of the solution to the transcutaneous device.

The volume of the second storage reservoir and/or the quantity of compressed fluid are adapted in order to have a substantially constant fluid pressure during a predetermined time period of the delivery. For example this predetermined time period may be at least 50% of the time period necessary to substantially drain the first storage compartment, preferentially at least 80%, more preferentially at least 90%, for example at least equal to the time period necessary to substantially drain the first storage compartment. In the latter case, the fluid pressure is constant over the entire duration of the delivery.

Body of the Indicator Device

The indicator device may comprise a body having a cavity in fluid or pressure communication with a fluid pathway via a fluid port or via an element configured to transmit the pressure to the plunger arranged into the cavity.

At least a part of the indicator device may be made of a transparent plastic, e.g. polypropylene (PP), polycarbonate (PC), polyethylene (PE), polyolefin, cyclo-olefin copolymer (COC) and cyclo-olefin polymer (COP). The internal surface of the cylinder may be coated, e.g. by PEG or silicone or parylene. Lubricant (e.g. silicone oil) may also be used to improve the plunger motion. The plunger(s) is (are) made of rubber or silicone or any other hard elastomeric material. Nevertheless, the friction of the plungers against the cavity wall may prevent undesirable movement of the plunger during handling of reservoir filling.

The first variable volume may be configured to receive a volume fraction of the solution intended to be infused to the patient, thus the wall material of this volume may comprise compatible material with the solution.

Movable Element

In some embodiments the movable element may be a plunger or other element which may be configured to move through/into the cavity of the indicator device. In order to simply the description, the document exposes the movable element as a plunger.

Figure 4:
FIG. 4 shows side-view of an example of a plunger with sealing lip at 45°.

The plunger may comprise lips configured to slide against the cavity wall and to provide a tight interface. For example, the plunger may exhibit a structuration or sealing lips to improve the tightness and/or to make the friction dependent on the direction of move. In another embodiment one plunger can only move in one direction (as shown by the FIG. 4). The orientation of the lips may be comprised between +90° and −90°.

A first embodiment of the indicator device comprises a single plunger. The single plunger (also called first plunger) may be configured to perform at least one motion through the cavity and more preferentially two motions through the cavity for example a forward and backward motion. The first plunger may be configured to move depending on the pressure of the solution intended to be delivered (depending on the fluid pressure in the drug reservoir).

The single plunger may be arranged into the cavity and may define a first variable volume between the first end of the cavity and the single plunger and a second variable volume between the second end of the cavity and the single plunger.

Initially, the plunger may be at a first initial position. When the solution pressure increases (caused by the activation of the delivery), the solution pressure induces a motion of the first plunger according to a first way, until it reaches a second position. Preferentially, in this phase, the first variable volume increases and the second variable volume decreases. The second position may be maintained as long as the solution pressure is within a determined range or greater than a determined value (which may be required for the flow of the solution to the patient). When the solution pressure decreases, a biasing means (compressed gas, spring . . . ) may move the first plunger according to a second direction (for example opposite to the first way, for example toward the first position) until a third position or the first position is reached. Preferentially, in this phase, the first variable volume decreases and the second variable volume increases.

A second embodiment of the indicator device comprises two plungers (or more, for example three). A first plunger may be configured to perform at least one motion through the cavity and more preferentially two motions through the cavity for example a forward and backward motion. The first plunger may be allowed to move depending on the pressure of the solution intended to be delivered.

The first plunger and the second plunger (and more) may be arranged into the cavity and may define a first variable volume between the first end of the cavity and the first plunger, a second variable volume between the first plunger and the second plunger, and a third variable volume between the second plunger and the second end of the cavity.

Initially, the first plunger may be in a first initial position. When the solution pressure increases (caused by the activation of the delivery), the solution pressure induces a motion of the first plunger according to a first way, to a second position. Preferentially, in this phase, the first variable volume increases, the second variable volume may stay constant or may decrease and the third variable volume may stay constant or may decrease. The second position may be maintained as long as the solution pressure is within a determined range or greater than a determined value (which may be required for the flow of the solution to the patient). When the solution pressure decreases, a biasing means (compressed gas, spring . . . ) may move the first plunger according to a second direction (for example opposite to the first way, for example toward the first position) to a third position or the first position.

Preferentially, in this phase, the first variable volume decreases, the second variable volume increases and the third variable volume stays constant. A second plunger may be configured to perform at least one motion through the cavity or two motions through the cavity for example a forward and backward motion. One motion of the second plunger may be caused by the pressure of the solution intended to be delivered and/or by the first plunger motion. For example, the solution pressure may cause a motion of the first plunger which pushes the second plunger along the same way. Initially, the second plunger may be at a first initial position. When the solution pressure increases (caused by the activation of the delivery), the solution pressure and/or the first plunger induces a motion of the second plunger according to a first direction, to a second position. The second position may be maintained as long as the solution pressure is within a determined range or greater than a determined value (which may be required for the flow of the solution to the patient). When the solution pressure decreases, a biasing means (compressed gas, spring . . . ) may move the second plunger according to a second direction (for example opposite to the first direction, for example toward the first position) to a third position or the first position. In another embodiment, the second plunger stays in its second position even if the solution pressure decreases at the end of the delivery.

At least one plunger comprises a surface on which the fluid pressure is applied. A surface of the first plunger may be configured to be in contact with the solution to be delivered. In this case, the solution applies a force (due to the fluid pressure in the drug reservoir) on this surface causing the plunger's motion.

The second plunger (12) may comprise a fluid pathway (such as a through hole or a porous element) which extends from one end of the second plunger to an opposite end of the second plunger for example according to an axis parallel to the axis of the elongated cavity (i.e. the axis of revolution for a cylindrical elongated cavity).

The plunger may be configured to slide against the elongated wall of the cavity. Furthermore, a sealing material (for example the plunger may comprise a sealing material) may be arranged between the plunger and the elongated wall of the cavity in order to provide a sealing interface between a volume defined downstream the plunger and another volume defined upstream the plunger.

Cavity of the Indicator Device

As described above, the indicator device comprises a body including a (internal) cavity which may have a fluid port adapted to be coupled to at least one reservoir and/or the transcutaneous device. The cavity further comprises a first end and a second end which define a main axis. The first end may comprise the fluid port.

The second end of the cavity may be connected to a communication port in fluid communication with the exterior environment of the device. This communication port may be closed (dead-end obtained using a plug or thermowelding, UV welding, over welding, US welding, overmolding . . . ). An initial air volume is therefore entrapped inside the cavity, for example at the atmospheric pressure, e.g. 1013 mbar absolute (1 atmosphere).

In some embodiments, the indicator device comprise at least one of a first fluid port in fluid or pressure communication with the medical fluid reservoir and a second fluid port in fluid or pressure communication with the pressurized reservoir.

One or more movable element is arranged movably into the cavity. The interior walls of the cavity and the movable element (a wall or a surface) define at least one variable volume.

In some embodiments, the indicator device comprise two distinct cavities, a first cavity in fluid or pressure communication with the medical fluid reservoir and a second cavity in fluid or pressure communication with the pressurized reservoir. The first cavity may be tightly separated from the second cavity.

Position of the Movable Element

The first movable element is configured to have at least two distinct positions: a first initial position and a second position. Preferentially, the first movable element is configured to move from the first initial position to the second position and then from the second position to the first initial position or to a third position.

The first movable element may be configured to reach the second position when the solution is flowing to the patient. The first movable element may be configured to stay at the second position over a substantial part of the duration of the solution delivery.

If the indicator device comprises two distinct movable elements, then the second movable element is configured to have two distinct positions: a fourth initial position and a fifth position. The second movable element may be configured to move from the fourth initial position to the fifth position and then stay at the fifth position. The second movable element may be configured to reach the fifth position when the solution is flowing to the patient. The second movable element may be configured to stay at the fifth position after the end of the solution delivery.

Stop Member

The indicator device may include a first mechanical stop (23) (also called stop member) that is used to define the plunger's position during infusion (see FIG. 6). After activation of the device the plunger shall reach the first mechanical stop which may be located in the dead-end side of the cavity, considering the worst specified pressure conditions. For instance, if the device is powered by a liquefied gas (e.g. butane), the worst conditions are met at the lowest specified temperature, which leads to the smallest value of the propellant vapour pressure and therefore the smallest value of the injection pressure $P_{inj}$. After activation, the gas initially present in the cylinder is compressed according to the Mariotte's law. The pressure $P_{comp}$ inside the volume of the cavity comprised between the first mechanical stop and the cylinder dead-end (during infusion) is function of the ratio of volume change and the temperature. It is assumed that the temperature and the pressure during the body and plungers assembly are well controlled (e.g. 1 atmosphere at 22° C.). It is also assumed that the environmental conditions during the device unpacking do not modify the initial plunger positions. For a temperature operating range [+5° C.; +40° C.], the variability of $P_{comp}$ is limited to ±6% if the first mechanical stop is reached by the plungers during infusion. This feature is important to secure the movement of the solid plunger back against a second mechanical stop at the end of the infusion, when $P_{comp}$ becomes the driving pressure. This second mechanical stop formed by a cylinder conical narrowing (or an inner ring) is shown in FIGS. 5 and 6.

A stop member may be the first end of the cavity or the second end of the cavity and may be arranged into the cavity, for example against the internal wall of the cavity or may be a magnet element (or ferromagnetic element) which cooperates with the movable element (comprising a magnet element or a ferromagnetic element) in a magnetic manner. A stop member may be dedicated to one or several movable element.

As disclosed in the FIGS. 5, 6, 12, and 13, the stop member (23) may be configured to stop at least one movable element and to allow the motion of at least one movable element according to a single direction. Thus, the motion of at least one movable element may be restricted to only one direction by a stop member.

Some figures (see e.g. the FIG. 7) do not show a stop member because it may be hidden by a part of the cavity body.

The stop member may be configured to prevent a displacement of a movable element as long as a pressure threshold is not reached, as described thereafter for example in the item "INDICATOR WITH THRESHOLD EFFECT".

Zeroing Magnet

Initialization/zeroing of the movable element positions may be performed using a magnet placed into the cylinder.—this magnet can be used as mechanical stop. The main drawback is the loss of MRI compatibility, except if the magnet is mechanically locked in production after movable element positioning.

Indicator with Threshold Effect

The indicator device may be configured so that the plunger may require a minimum pressure to initiate its displacement. Thus, for example during the filling of the drug reservoir, even if a pressure is generated (for example due to the filling), this pressure is not enough to initiate the plunger motion. It could be interesting to no change the plunger position during this phase. The initial displacement may be secured by the large pressure generated during the device activation, the pressure forces onto the plunger being much larger by design to friction forces.

The plunger may be able to reach a position after activation (right part of the cavity). During the final pressure release, when the liquid in the communication port is no longer pressurized, the plunger may move toward its initial position without reaching it due to this threshold effect.

This threshold effect may be obtained by:

Friction between the cylinder and the plunger:
   Friction controlled by the tolerances between the cylinder and the plunger diameters
   Friction controlled by structuration of the cylinder and/or the plunger
   Friction controlled by the presence of sealing lips (see e.g. FIG. 4)
Friction due to the inner shape of the cylinder or the outer shape of the plunger (see e.g. FIG. 5)

The FIG. 5 show an embodiment of an infusion status indicator comprising only one plunger. The presence of a conical narrowing in the inner part of the cavity allows the definition of three different positions of the plunger:

Initial position=plunger in the right part of the cavity
Infusion position=plunger in the left part of the cavity
End of infusion position=plunger in an intermediate predefined position (conical narrowing)

The FIG. 5d shows an example of windows arranged on the body of the indicator device that allow visualizing and therefore determining in an unambiguous way the injection status.

Filling Phase

The indicator device may be configured to indicate to the user an indication relative to the filling phase. A position of a movable element may be reached when a sufficient amount of solution has been filled into the drug reservoir.

In some embodiments shown by the FIGS. 23a to 23f, an indicator device (2) may comprises an indication of the filling end. In this example the indicator device (2) further comprises four different states/positions (of one or more movable elements). A first plunger (11) (for example a solid first plunger) and a second plunger (12) (for example a drilled plunger) are located inside the cavity. Preferentially, the delivery system (not shown) comprises furthermore a valve device (not shown) such as an anti-free flow valve having a predefined opening threshold (as described thereafter), said predefined opening threshold being substantially larger than the maximum reservoir pressure generated during the reservoir filling.

Three volumes are defined: a first variable volume between the first plunger (11) and the first end of the cavity (14), a second variable volume between both plungers (11, 12) wherein a biasing means (29) (such as a compressible spring) may be arranged (and acts on both plungers) and a third variable volume between (15) the second plunger (12) and the second end of the cavity). Optionally, the third variable volume may be vented via a venting device (28). The two plungers are initially placed on the right of a stop member (23).

If the delivery system (1) is initially empty, the user has to fill the drug reservoir (5). For this purpose, the drug reservoir may comprise an inlet port (38) in fluid communication with the internal compartment of the drug reservoir (as disclosed by the FIG. 1). The user may use a syringe to fill the drug reservoir (5) with the solution.

Position 1 (FIG. 23a): before filling, the biasing element (29) maintains the two plungers against the stop member (23) and the first end of the cavity (14). If the indicator device comprises a windows arrangement of the FIG. 23e, only the second plunger (12) is visible through the window 1. If the indicator device comprises the window arrangement of the FIG. 23f, only the first plunger (11) is visible through the window 1. In another embodiment, none of the first or second plunger may be visible through any window before filling of the reservoir.

When the user fills the drug reservoir, the solution initially stored into the syringe is moved inside the drug reservoir. The membrane (7) moves depending on the injected volume into the drug reservoir.

Position 2 (FIG. 23b): after filling; the first plunger (11) becomes visible through the window 2. The reservoir is designed such as to generate a slight pressure $P_{fill}$ after filling. This pressure will move the solid plunger leftwards and compresses the spring. The stiffness of the spring is adjusted such as to allow the first plunger to reach the protrusion of the second plunger.

In order to generate a sufficient pressure into the drug reservoir during the filling (or at the end of the filling), the injected volume of solution may be greater than the volume of the internal compartment of the drug reservoir. In this case, the capacity of the internal compartment of the drug reservoir may be configured in such a manner that the filling end is characterized by a peak of pressure in the drug reservoir which allows the first plunger to reach a determined position.

Optionally, the pressure may further be generated due to the elasticity of the membrane. In this case, the elasticity of the membrane may be configured in such a manner that the filling end is characterized by a peak of pressure in the drug reservoir which allows the first plunger to reach a predetermined position.

Position 3 (FIG. 23c): during infusion (after activation of the delivery), both plungers move leftwards due to the large injection pressure $P_{inj}$ that is able to overcome the stop member's obstruction. If the delivery system comprises a valve device, the valve device opens the fluid pathway allowing the solution to flow to the outlet device.

Figures 23E, 23F:
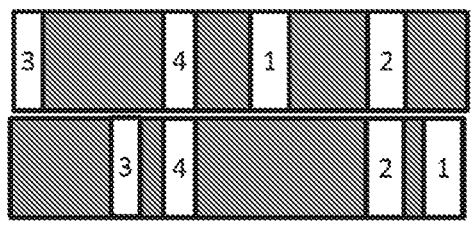

If the indicator device comprises the window arrangement of the FIG. 23e, only the second plunger (12) is visible through the window 3. If the indicator device comprises a windows arrangement of the FIG. 23f, only the first plunger (11) is visible through the window 3.

Optionally, the second plunger (protrusion of the second plunger) may be configured to maintain the first plunger into a determined position during this phase and/or to prevent an over-compression of the spring. The second plunger may comprise a through hole providing a pressure equilibration or a fluid communication between the second variable volume and the third variable volume.

Position 4 (FIG. 23d): after infusion; the first plunger (11) is now visible through the window 4. The pressure in the cavity containing the drug drops to zero at the end of the infusion. Due to the action of the spring, the first plunger moves rightwards until reaching the stop member (23).

In this example, the FIGS. 23e and 23f show two distinct window arrangements. The window arrangement of the FIG. 23e provides a set of windows allowing the first plunger and the second plunger to indicate a status of the delivery system. The window arrangement of the FIG. 23f provides a set of window allowing only one plunger (for example the first plunger) to indicate a status of the delivery system.

In another embodiment as shown by the FIGS. 28a, 28b, 28c, 29a and 29b, the delivery system (201) comprises a housing (202), an internal compartment such as a cavity (203), a reservoir module (204), and a fluid pathway (205). The module reservoir may comprise at least one of the first reservoir, the second reservoir and the third reservoir as described in this document.

Preferentially, the delivery system (201) comprises one or more vent devices (207). The vent device (207), also referred to as an opening, a vent or a vent port may be provided to direct air into the housing to enable pressure equilibrium within the interior of the device. The vent device may further enable air flow regulation (e.g., according to pressure changes) to perform pressure equilibration and/or enable air (including oxygen) transfer to one or more elements of the device that require communication with ambient air, at least in part, to operate. Such one or more elements may include a power supply (such as a zinc-air battery), an indicator device (209) (see FIG. 30a).

In some embodiments, a selective membrane (such as a hydrophobic membrane layer) may cover the vent device (207) to prevent water from entering into the delivery system or the cavity. In some embodiments, at least one vent device is provided in the proximity of at least one of the reservoir module (204), an indicator device (209) and power supply (212).

The fluid pathway (205) may comprise at least one of a pumping device, a needle (206), a pressure transducer, and other element (such as sensor, filter, . . . ). In order to simplify the description, the term "needle" is used to refer to the outlet device of the delivery system. The outlet device may be a needle, a transcutaneous device or port intended to be connected to a transcutaneous device.

The reservoir module may comprise a first reservoir (also called drug reservoir as described in this document) intended to be filled and/or to store a solution (as described above). The first reservoir may comprise a movable wall (such as a flexible membrane, a plunger) defining at least in part the internal compartment of the first reservoir. The first reservoir may comprise two movable walls sealed together (for example two flexible membranes) defining at least in part the internal compartment of the first reservoir. The first reservoir may comprise a movable wall (for example a flexible membrane) and a rigid wall sealed together and defining at least in part the internal compartment of the first reservoir. The first reservoir may further comprise one or more fluid port (for example an inlet port and/or an outlet port) intended to allow a filling process of the internal compartment (used as an inlet port) and/or to allow a fluid communication with the fluid pathway (used as an outlet port). A filter may cover an outlet port of the first reservoir, for example, arranged into the internal compartment.

The reservoir module may further comprise a pumping device configured to move the solution stored into the internal compartment of the first reservoir for example by applying a positive pressure to the first reservoir (pressurized gas, liquefied gas, spring applying a force wall of the reservoir, . . . ). The pumping device may comprise a second reservoir (as described in this document) having a movable wall which exerts a force onto the movable of the first reservoir.

Figure 28C:
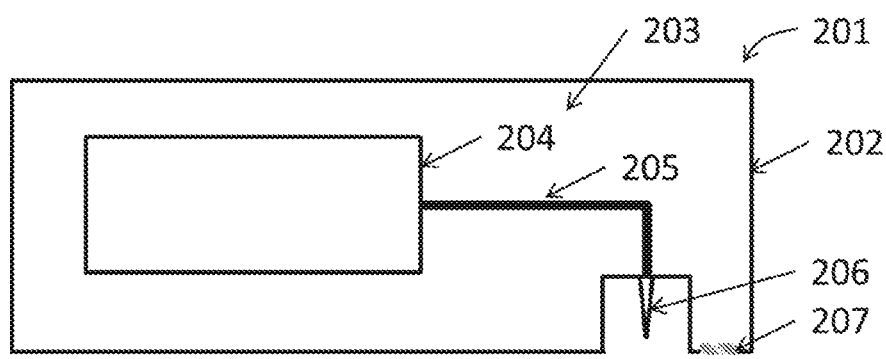

The FIGS. 28a, 28b, 29a, and 29b show a delivery system comprising a removably occluding device (208) intended to occlude at least one of the vent device (207) and the needle (206). The FIG. 28c shows the same delivery system but after removing the occluding device (208). The removably occluding device (208) may comprise a first part configured to maintain the needle in a sterilized state and a second part configured to close the vent device. For example the first part may comprise or form or close a cavity in which the needle is kept sterilized. And the second part may comprise a sealing surface in order to hermetically seal the internal compartment of the housing (for example the cavity).

Figure 30B:
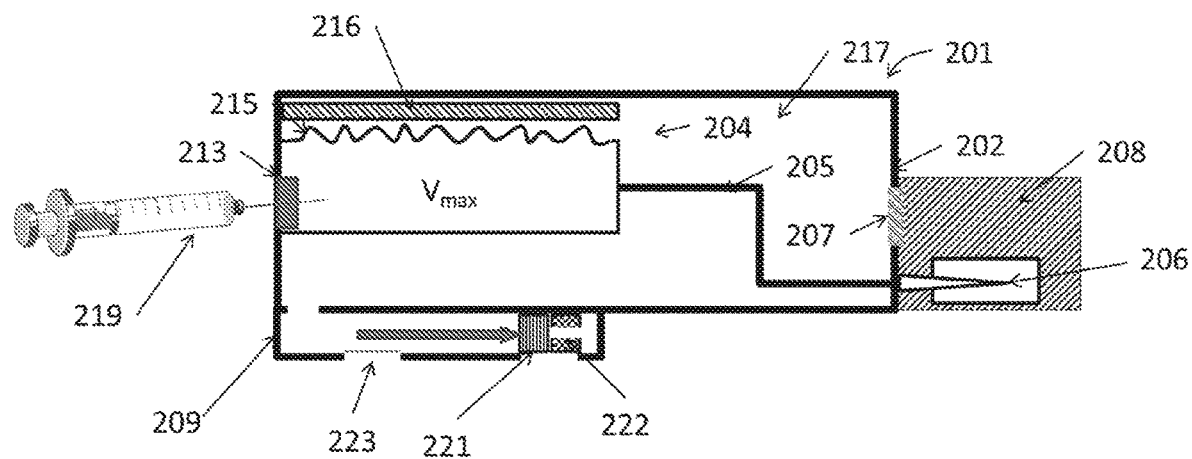
Figure 30C:
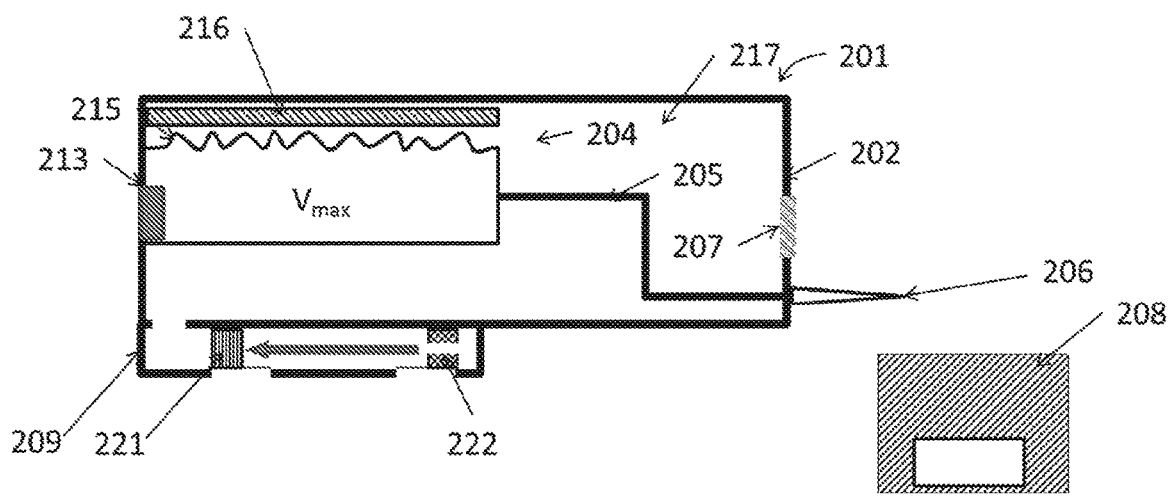

According to the FIGS. 30a, 30b, and 30c, the indicator device comprises at least one movable element (for example one or more plunger (221, 222)) and a cavity in which the at least one movable element may move. The at least one movable element (221, 222) may divide the cavity of the indicator device into two distinct volumes (a first volume (224) and a second volume (225)). The at least one movable element (221, 222) may provide a hermetic separation between the first volume (224) and the second volume (225). The first volume (224) and/or the second volume (225) may be defined by at least one of the wall of at least one of the cavity and the movable element (for example a first plunger). The first volume (224) and/or the second volume (225) may be configured to increase and/or decrease as the movable element moves into the cavity of the pressure transducer.

Preferentially, the first volume (224) is in pressure communication with at least one of the first cavity (217), the fluid pathway (205), and at least one reservoir of the reservoir module (204). For example, the indicator device may further have a fluid port (such as a first opening (226)) providing fluid communication between the first cavity (217) and the first volume (224) of the indicator device cavity. A first plunger (221) may comprise a wall having a first surface subjected to the pressure present into the first cavity (217). A second plunger (222) may be arranged into the cavity of the indicator device (209), for example into the second volume (225). The second plunger (222) may be configured to move into the cavity for example pushed by the first plunger. The second plunger may comprise fluid communication means (such as a through hole) configured to prevent the second volume into two additional volumes hermetically separated. The indicator device (209) disclosed by the FIGS. 30 a, b, and c is a potential embodiment and it may be replaced by another indicator device described in this document and vice-versa.

The indicator device may comprise at least one window (223) configured to show the position of at least one plunger into the cavity of the indicator device (209). A first opening and/or position (of the at least one plunger) may provide information related to a first state of the delivery system or reservoir.

According to the FIG. 30a, before the filling process, the volume of the internal compartment of the reservoir is minimal and the at least one plunger is in a first position into the pressure transducer. A first window may show the position of the at least one plunger. During the filling process, the pressure into the first cavity (217) increases and transmits this pressure into the first volume as the reservoir is filled. The at least one plunger moves as the pressure increases and/or as the reservoir is filled. According to the FIG. 30*b* at the end of the filling process, the volume of the internal compartment of the reservoir is maximal and the at least one plunger is in a second determined position into the pressure transducer. A second window may show the position of the at least one plunger. According to the FIG. 30*c*, once the filling process has been ended, the filling device (219) may be removed and the removably occluding device (208) is removed.

Once the removably occluding device (208) has been removed, the overpressure present into the first cavity may exit through the vent device (207). In some embodiments, the second volume (225) may be hermetically closed and/or comprise a biasing means and may cause a back motion of the at least one plunger (for example the first plunger (221)) as the overpressure exits through the vent device (207). In some embodiments, the at least one plunger may comprise a second plunger (222) (as described above), if the second plunger comprises a fluid communication means, only the first plunger (221) may go back to or in the direction to the first position. In this case, the second plunger may substantially stay in the second position.

A similar embodiment has been disclosed by the FIG. 31 which show several views of a potential indicator device (or filling gauge) which may be used with the system described in this document. An example of another potential system has been described by the EP patent application EP18182850.0, which is incorporated by reference in the present application. In this embodiment, the indicator device (209) or the visible part of the indicator device (209) is located on the bottom of the device and thus it may be visible only during the filling process. As shown in the FIGS. 31*a*, *b* and *c*, the fill volume may be indicated by the position of a plunger. The FIG. 31*a* shows two plungers (221, 222) at the left of the indicator, before the filling. The FIG. 31*b* shows two plungers (221, 222) at the right of the indicator, just after the filling before to remove the occlusion device from the vent device. The FIG. 31*c* shows a first plunger (221) at the left of the indicator and a second plunger at the right (222), after the occlusion device removal. A textual indication or gradual indication may indicate the fill volume by the second plunger.

In some embodiments, the indicator device may provide an indication relative to the filling (of the first reservoir) and to the delivery. In some embodiments, the indicator device comprise a first side and a second side, the first side may be configured to provide an indication relative to the filling and the second side may be configured to provide an indication relative to the delivery. The FIGS. 32 to 35 show several embodiments comprise such features.

Figure 32E:
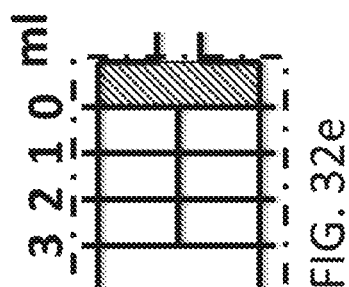
Figure 32E:
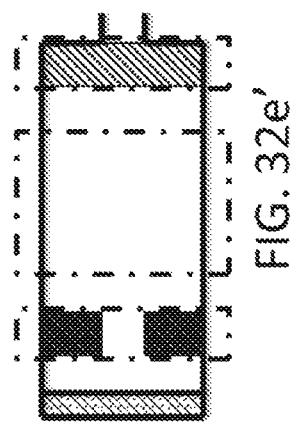

For example, the FIGS. 32*a*, 32*b*, 32*c*, 32*d*, and 32*e* show a first side (301) of the indicator device (300) which may provide an indication relative to the filling of a first reservoir while the FIGS. 32*a'*, 32*b'*, 32*c'*, 32*d'*, and 32*e'* show a second side (302) of the indicator device (300) which may provide an indication relative to the delivery. Each side comprises at least one of a visual element (305) and an indicator window (306). The FIGS. 32*a*, 32*b*, and 32*c* show the motion of the first and second movable elements (303, 304) (also called plungers) during a filling of the first reservoir. The indicator device may comprise a first end (308) and a second end (309) which define a main axis (310). The indicator device (300) may further comprise a fluid port (307) coupled to at least one of the first reservoir and the transcutaneous device (or other as described in some embodiment in this document). The delivery system (not shown) may comprise a vent device and a dedicated removably occluding device (as described above).

The delivery system may be configured in such manner to prompt the user to expose the first side of the indicator device during the drug filling. For example, the delivery system may comprise an upper face and a lower face. The lower face may comprise an inlet port of the first reservoir and may expose the first side (301) (for example a first visible face or surface) of the indicator device (300) while the upper face may expose the second side (302) (for example a second visible face or surface). An example of such delivery system is shown by the FIG. 37. According to this embodiment, the delivery system (400) may comprise a reservoir module (407) (as described above) an inlet port (403). The delivery system may comprise a first face (401) (for example a lower face) and a second face (402) (for example an upper face). In this example the first face is opposite to the second face but other arrangements may be possible. The first face (401) may expose a first side (405) of the indicator device (404) and the second face (402) may expose a second side (406) of the indicator device (404). The first face may further comprise an access to the inlet port (403). Thus, during the filling process, the user may have to turn the delivery system on its back. In this position the inlet port and the first side may be viewed by the user but not the second side. In other terms, when the first side can be seen by the user the second side may be hidden or cannot be visible and/or when the second side can be viewed by the user the first side may be hidden or cannot be visible.

The FIGS. 32*a* and 32*a'* show the position of the first and second plunger before the filling process. During the filling process (see FIGS. 32*b* and 32*b'*), the volume of the first reservoir increases but since the interior of the delivery system cannot be vented by the vent device (due to the removably occluding device as described above), the pressure in the first reservoir and/or in the interior of the delivery system increases. This pressure increase induces a motion of the first and the second plungers. The position of the first and the second plungers relatively to the visual element (text, icon, symbol, graduation, . . . ) may provide an indication relative to the filling volume (for example here 3 ml). At the end of the filling process (see FIGS. 32*c* and 32*c'*), the removably occluding device may be removed and at least one of the first plunger (303) and the second plunger (304) performs a back motion (for example until the initial position or until a determined position). This back motion may be caused by a biasing means for example a pressurized gas, a spring, biasing element, . . . .

For example, if the volume defined between the second end (309) and at least one of the first plunger (303) and the second plunger (304) is sealed, the air or gas trapped in this space may be pressurized at least due to the first motion and acts as a counterforce (other embodiment of this indicator device is possible as described in this document). Thus, when the removably occluding device is removed from the vent device, the pressure in the first reservoir and/or in the interior of the delivery system is balanced with the external environment of the delivery system. The pressure of the trapped air/gas induces the back motion of at least one of the first plunger (303) and the second plunger (404). If the second plunger comprises a through hole (as shown by the FIG. 32) only the first plunger performs a back motion.

The FIGS. 32*c* and 32*c'* show the indicator device (300) which provides the following information: "The (first) reservoir is filled and the delivery system is ready to be used".

In order to prevent a misinterpretation, the position of the plungers at the end of the filling process may be different than the position of the plungers when the delivery system infuses. The delivery system may be configured for example to generate more pressure during the delivery and thus may provide another position to at least one of the first plunger and the second plunger.

Figure 32D:
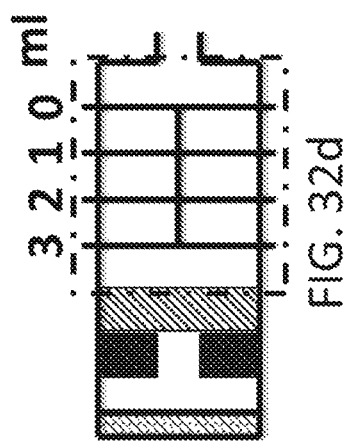
Figure 32D:
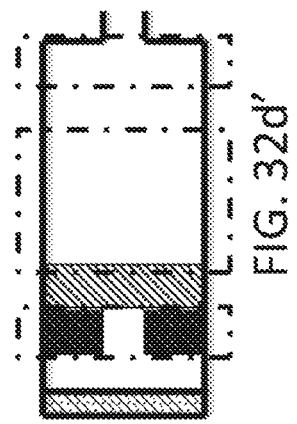

The FIG. 32*d'* shows the indicator when the delivery system is delivering the solution to the patient. The FIG. 32*e'* shows the indicator device at the end of the delivery.

The FIGS. 33 to 35 show similar features. The main difference is that the indicator device may comprise a fluid pathway (311) which allows a fluid communication between two volumes separated by the second plunger. The FIG. 33 show a plunger which may be pierce by a needle (310). The FIGS. 34 and 35 show a fluid pathway (311) arranged in the body of the indicator device, for example at the second end, in order to bypass the second plunger.

Visual Element and Indicator Window

The indicator device (and/or the housing of the delivery system) may comprise a window configured to allow at least one of the first plunger and the second plunger to be visible from the outside of the body or housing of the delivery system. The window is arranged in such a manner that at least one of the first plunger and the second plunger is visible in a predetermined position.

A dual visual element (for example at least two distinct plungers or with a compressible visual element) with window(s) may be a robust solution since the visualization of both plungers at the end of the infusion is an assurance of the total injection of the drug.

The window(s), the visual indicator and/or the cavity (internal wall of the cavity) may be coloured to improve the injection status monitoring. The FIG. 7 shows an example of indicator comprising a second plunger (12) associated with a first plunger (11). Only two windows (24) are used here. Before injection no plunger (11, 12) is visible. After activation the second plunger (12) is visible. The first plunger (11) becomes finally visible after the infusion completion (the mechanical stoppers are not shown in the FIG. 7).

The indicator device may comprise markers to identify the infusion status. These markers may be a text, an icon, a colour, other visual means . . . . These markers may be made by pad printing, ink jetting, or laser marking, sticker . . . .

The indicator device may comprise a longitudinal window (24) along the cylinder to verify the plunger's positions at all time and therefore check eventual failure. This feature is notably useful in production to verify the correct initial positioning of the plungers (11, 12). This feature may be used to distinguish the initial status (no plunger visible) and the intermediate or faulty status that corresponds to the two plungers (11, 12) located in between the two vertical observation windows. The movement of the plunger may be slow (notably in case of viscous drug infusion) and therefore the time necessary to reach the first mechanical stop (also called stop member) (23) may be substantially long.

Alternative solutions may include a single window (24) with marker to identify the infusion status.

As disclosed by the FIG. 9, the system may include two "solid" plungers (11, 12) and a cylinder with both ends open. The two plungers are not initially in contact as illustrated in the FIG. 9*a*. The plunger (12) that is not in contact with the liquid to be infused moves against a mechanical stop (which may be the second end of the cavity) while the plunger in contact with the liquid moves up to an intermediate position. The compression of the air in between the plungers allows the backward motion of the plunger (11) in contact with the liquid, limiting the dead volume of the device as shown in the FIG. 9. This later configuration is notably useful for the placement of the plungers in production.

Three solid plungers having different colours may be used, each plunger being only visible during one predefined phase of the injection. A typical example of realisation is shown in the FIG. 11. In another embodiment, two plungers are used but at least one of them comprises two distinct colours.

In all embodiments the window(s) may be tinted to improve the distinction between the different infusion states.

The second plunger (12) may be substituted by a compressible visual element (31) as shown by the FIG. 10. In this embodiment, the indicator device may comprise a single window.

The different proposed embodiments may be combined to form alternative solution for the injection status indicator.

The window may comprise a color filter in order to change the perception of plunger color. For example, the plunger may be yellow, a first window may comprise a blue filter and a second window may comprise a magenta (or red) filter. If the plunger is located below the first window, the user sees a green color and if the plunger is located below the second window, the user sees a red (or orange) color.

The FIG. 24 show several external views of a potential infusion status indicator (2) which may be used with the system described in this document. An example of a potential system has been described by the EP patent application EP18182850.0 or EP19151324.1. FIGS. 24*a, b,* and *c* show an illustrative version of this indicator as seen on the top shell of the device (for example). This purely mechanical infusion status indicator may have at least one of the following three different states:

One dot: Ready to inject (FIG. 24*a*),
Two dots: Injection on-going (FIG. 24*b*)
Three dots: End of injection (FIG. 24*c*).

The "end of injection" indication may be only visible when the reservoir membrane is fully collapsed against the bottom of the reservoir shell. It is not visible in case of cannula occlusion. For a specific medication volume and viscosity, maximum infusion duration will be indicated in the user manual, therefore the user can deduce that the full volume has not been administered (in case of total occlusion for instance) if the infusion status indicator is still showing "injection on-going" after this maximum duration. The high pressure generated by the propellant vapour will limit the occurrence of an occlusion in the cannula.

Biasing Means

The biasing means may be a spring, a compressible gas or an elastic element. The biasing means is used to move back the first plunger to it final position, for example from the second position to the third position or to the first position.

Some embodiments (described in this document) use air (trapped, gas, pressurized gas, . . . ) as a biasing means to move back the plunger in contact with the liquid at the end of the infusion. An alternative embodiment uses a compression spring (25) located inside the cylinder to that end. A typical example is provided in the FIG. 12. The infusion status indicator comprises here a second plunger (12), a green plunger (11) and a compression spring (25) in between. The second plunger (12) may be drilled for initial placement purpose, so as to prevent the generation of a pressure between the plungers during the assembly. Before infusion only the second plunger (12) may be visible in the first window (24) 1. After activation the pressure of the liquid pushes the first plunger (11) and also the second plunger (12) via the compression of the spring. The infusion is on-going when the second plunger (12) is visible in the second window (24). Finally the drug pressure release at the end of the infusion induces the backward movement of the first plunger (11) which becomes visible in the third window (24). A mechanical stop (23) (conical narrowing of the cylinder) may be used to secure the final position of the first plunger after infusion.

An alternative embodiment may comprise a single spring (25) and plunger (11) inside a cylinder with one stop limiter (23) as illustrated in the FIG. 13. The mechanism is similar to the one described in the FIG. 5, through the restoring force that is used for the backward movement of the plunger after infusion is no longer compressed air but a compression spring. The plunger can be seen iteratively in each of the 3 windows shown in the FIG. 13d, depending on the infusion status (ready to inject, injection on going and end of infusion).

The FIGS. 36a, 36b and 36c show different positions of the first and the second plunger wherein the biasing means (312) may be spring device which pushes the first plunger against the first end. The FIGS. 36d, 36e and 36f show different position of the first and the second plunger wherein the biasing means may be spring device which pull the first plunger to the first end.

The FIG. 38 shows a delivery system comprising a first reservoir (501) (having a movable wall) in fluid communication with a patient (504) via a fluid pathway (503). The delivery system further comprises a second reservoir (502) storing a pressurized fluid and being configured to apply a pressure on a movable wall of the first reservoir (501), and an indicator device (500). The indicator device is in fluid or pressure communication with at least one of the first reservoir and the second reservoir via dedicated fluid port. As described above, the indicator device may comprise a cavity, a first movable element (507), and a second movable element (508). In this case, the fluid pressurized may be used to perform the back motion of the first movable element (507). Nevertheless, if the pressurized fluid applies at the same time the pressure on the movable wall and in the cavity of the indicator device (as soon as the delivery is triggered), no motion may occur. Thus, the pressurized fluid has to be controlled in order to allow a first motion of the first movable element.

In some embodiments, the indicator device or the delivery system may comprise a valve control (506, 506'), in order to prevent the pressurized fluid to apply a pressure to the indicator device too early. In a first embodiment, the valve control may comprise a valve (506) which controls the flow of the pressurized fluid through the fluid pathway (505) which connects the second reservoir to the indicator device (500). In a second embodiment, the valve control may comprise an assembly (506) having a needle and a pierceable wall. The needle may be arranged with the second movable element (508) in such a manner to allow a fluid communication when the second movable element is pushed against the pierceable wall. Both embodiments are show by the FIG. 38 but the valve (506) and the assembly (506') may be two distinct embodiments of the valve control.

Anti-Free Flow Valve

Reservoir filling, whatever the nature of the reservoir itself, may pressure the drug and generate a free-flow. To prevent this undesirable flow (free flow) of drug (which may be problematic if the filling is made before the placement of the device onto the patient and the introduction of a cannula or a needle into the patient's skin), it is first proposed to use the plunger (11) in contact with the liquid as a valve device. The FIG. 14 shows an example of plunger having a protrusion or a shape (a conical shape) which allows blocking the flow as long as the pressure of the drug does not exceed a predefined value (which may depend on plunger friction against the inner wall of the cylinder and on the surface of the plunger that is submitted to the drug reservoir pressure after activation). At the end of the infusion the valve may be again in closed position if no mechanical stop is used (see e.g. FIG. 5 for a typical example of mechanical stop for the backward movement of the plunger).

Focus on the FIG. 14, the T-shaped channel as described above comprises a third fluid port in fluid communication with the outlet device (for example to the needle). This third fluid port may exhibit a conical shape to improve the tightness of this valve at low pressure.

Such a valve is an alternative to classical solution to block the flow at low pressure, including the use of a hydrophobic porous media, a mitral valve . . . between the reservoir and the needle.

An alternative embodiment exhibits a needle that is off-axis of the cylinder as shown in the FIG. 15. The schematic cross-section of the device is shown except for the off-axis needle that is entirely represented for sake of clarity. The solid plunger (11) that is intended to be in contact with the liquid blocks the flow from the reservoir to the needle until the drug pressure exceeds a predefined threshold value.

The FIG. 15 shows a fluid pathway without a T-Shaped channel. The first end of the cavity comprises:
  a first fluid port providing a fluid communication between the outlet of the reservoir and the cavity and acts as an inlet, and
  a second fluid port providing a fluid communication between the cavity and the outlet device and acts as an outlet, The fluid pathway is divided in two parts: a first part upstream of the cavity and a second part downstream of the cavity.

The indicator device is further used as a valve device which closes the fluid pathway when the fluid pressure is lower than a determined threshold. The valve may be closed before the activation of the delivery and after the end of the infusion, thanks to the forward and backward motion of the first plunger.

Anti-Free-Flow Valve with Controlled Opening Threshold

The FIG. 16 shows another embodiment of the present disclosure. This device is similar to the one disclosed in the FIG. 1 except for the presence of a valve device (3) (also called valve) in front of the needle inlet. This valve may comprise an additional (movable) plunger (32), a valve cavity (37) initially filled with compressible gas (for example air), and/or a plug (27). At rest (before activation of the device), the top surface of the plunger (32) is partly submitted to the pressure inside the communication chamber since mechanical stops (26) (also called plunger stoppers) are used to that end. This plunger itself may exhibit a structuration or texturizing that also leads to the same effect. During assembly, the introduction of the plug leads to the compression of the air comprised inside the cavity. It becomes possible to adjust the pretension (or opening threshold) of the valve by controlling by design the pressure inside the cavity in production, e.g. by introducing a plug having a well-controlled volume such as to generate always the same initial pressure inside the cavity. The activation of the device leads to the generation of a large pressure in the reservoir. This pressure will push against the top surface of the second solid plunger and will move it perpendicularly to the direction of the needle, freeing the fluid pathway through the needle. At the end of the infusion the second plunger will close again the inlet of the needle.

The opening threshold is typically larger than the maximum pressure that can be generated during filling in normal situation. The opening threshold may be adjustable using a threaded plug that is more or less screwed according to the target value of the valve pretension.

An alternative embodiment comprises a compression spring inside the cavity, said cavity being vented. The pretension may again be adjusted by controlling the initial spring compression, e.g. using a threaded plug that will used to control the initial length of the compression spring, as shown in the FIG. 17 wherein the plug is also vented.

Crack Valve

In another embodiment, the communication chamber comprises a flexible membrane in front of the inlet of a needle having both ends bevelled as shown in the FIG. 18. The flexible membrane will be pierced by the needle if the reservoir pressure exceeds a predefined value, freeing the fluidic pathway for the drug. The membrane is made of an elastomeric material to allow a large deflection and prevent a crack before the piercing by the needle.

In another embodiment the membrane cracks by the sole application of the pressure (mechanical failure due to the excess of strain induced by the large applied pressure after activation), the needle having a single bevel at the outlet (see the FIG. 19).

In another embodiment the valve is a plunger (32). As shown in the FIG. 20, a solid plunger (32) is placed in a second cylinder in direct communication with the needle inlet and the communication port. The activation of the device leads to the piercing of the plunger by the needle as illustrated in the FIG. 21. The plunger may be partially introduced into the needle in production to limit the dead volume of the device by reducing the size of the volume between the plunger (of the valve) and the needle). Moreover, it also prevents the injection of a large air volume in the patient at the beginning of the injection. As a compressible gas volume may be trapped in the valve cavity (37) at the end of the infusion, the plunger may move toward it initial position and block the flow. The compressible gas may be substituted by a biasing element such as a spring . . . .

Leakage/Failure Detection

In some embodiments, the indicator device may be configured to indicate a failure or leakage event of a pressurization means, in the case where the delivery system comprises such pressurization means.

The FIG. 39 shows a delivery system which may comprise at least one of a first indicator device (510) and a second indicator device (520). The first indicator (510) device may be configured to provide an indication relative to a status of the first reservoir (501) for example the delivery status of the fluid stored in the first reservoir (501) and the second indicator device (520) may be configured to provide an indication relative to a status of the second reservoir (502) for example a failure or leakage event of the second reservoir (502). The first indicator device may comprise the same features of the indicator device described in this document. The second indicator device may comprise a body (which may be an extension of the first indicator device's body) having an internal cavity. The internal cavity may comprise a first end and a second end which define a main axis of the cavity. A movable element (521) may be configured to move through the internal cavity depending on the pressure of the pressurized fluid of the second reservoir (502) after the trigger of the delivery system.

Once the delivery system triggered the pressurized fluid induces a first motion of the movable element (521) to a determined position. If no failure or leakage event occurs, the movable element has to stay at this position (until and/or after the end of the delivery). In case of failure or leakage event (for example a leakage of the pressurized fluid), the movable element will perform a back motion for example when the pressure of the pressurized fluid is less than the force of the counter-force (biasing means) (523). The biasing means may be a spring or other element disclosed in this document (air trapped, gas, . . . ). The indicator device (530) is an embodiment comprising in the same body the first and the second indicator device (510, 520).

The invention claimed is:

1. An indicator device for indicating an infusion status of a medical device adapted to deliver a solution stored in a reservoir to a patient, the indicator device comprising:
   a body;
   an elongated cavity in the body and having a first end and a second end;
   a first plunger configured to move relative to the elongated cavity and arranged into the elongated cavity dividing the elongated cavity in a first variable volume and a second variable volume, the first plunger configured to adapt different positions including,
      a first initial position which indicates a state before infusion,
      a second position which indicates a state during infusion, and
      a third position which indicates a state at the end of the infusion; and
   a port providing a pressure communication between the reservoir and the elongated cavity such that the first plunger moves depending on a pressure of the solution intended to be delivered, and such that the second position is reached due to an increase of a pressure of the reservoir and that the third position is reached when the reservoir is substantially empty.

2. The indicator device according to claim 1, further comprising:
   a second plunger configured to move relative to the elongated cavity, the second plunger moves through the second variable volume.

3. The indicator device according to claim 2, wherein the second plunger performs a motion caused by a forth motion of the first plunger.

4. The indicator device according to claim 2, wherein the second plunger comprises a through hole.

5. The indicator device according to claim 1, wherein the first plunger is configured to perform a back-and-forth motion.

6. The indicator device according to claim 1, wherein a first volume is in pressure communication with the reservoir storing the solution intended to be delivered.

7. The indicator device according to claim 1, further comprising: a position indicator window disposed on an exterior surface of the indicator device and configured to provide an external visual indication of the different positions of the first plunger.

8. The indicator device according to claim 1, further comprising: a biasing device configured to induce a back motion of the first plunger.

9. The indicator device according to claim 1, wherein the indicator device is configured to indicate at least one of the following states:
   before infusion,
   during infusion,
   at the end of the infusion,
   before reservoir filling, during reservoir filling,
at the end of the reservoir filling,
a failure, and
a leakage.

10. A medical device adapted to deliver a solution to a patient, the medical device comprising:
a pressurized reservoir for storing the solution;
an indicator device including,
  a body,
  an elongated cavity in the body and having a first end and a second end, and
  a first plunger configured to move relative to the elongated cavity and arranged into the elongated cavity dividing the cavity into a first variable volume and a second variable volume, the first plunger is configured to adapt different positions including,
    a first initial position which indicates a state before infusion,
    a second position which indicates a state during infusion, and
    a third position which indicates a state at the end of the infusion,
  a port providing a pressure communication between the pressurized reservoir and the elongated cavity such that the first plunger moves depending on a pressure of the solution intended to be delivered such that the second position is reached due to an increase of a pressure of the reservoir and that the third position is reached when the pressurized reservoir is substantially empty,
an outlet port in fluid communication with the patient; and
a fluid pathway from an interior of the pressurized reservoir to the outlet port,
  wherein the indicator device is in pressure communication with the fluid pathway.

11. The medical device according to claim 10, wherein the indicator device further comprises:
a valve device configured to prevent the solution from reaching the outlet port.

12. The medical device according to claim 11, wherein the valve device is a part of the first plunger which occludes the fluid pathway when the first plunger is in a predetermined position.

13. The medical system according to claim 10, further comprising:
a housing defining an internal cavity accommodating the pressurized reservoir and a vent configured to vent the internal cavity of the housing.

14. The medical system according to claim 13, further comprising:
a removably occluding device configured to occlude the vent at least during a filling process of the pressurized reservoir or a storing period.

* * * * *